US012708485B2

(12) United States Patent
Pennington, III

(10) Patent No.: US 12,708,485 B2
(45) Date of Patent: Aug. 18, 2026

(54) SYSTEM FOR TRACKING TAGGED SURGICAL ARTICLES WITH A TRANSPORT CONTAINER TRACKING ASSEMBLY

(71) Applicant: Howmedica Osteonics Corp., Mahwah, NJ (US)

(72) Inventor: Fred Paul Pennington, III, Murfreesboro, TN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 18/701,292

(22) PCT Filed: Oct. 13, 2022

(86) PCT No.: PCT/US2022/046538
§ 371 (c)(1),
(2) Date: Apr. 15, 2024

(87) PCT Pub. No.: WO2023/064448
PCT Pub. Date: Apr. 20, 2023

(65) Prior Publication Data

US 2024/0415608 A1 Dec. 19, 2024

Related U.S. Application Data

(60) Provisional application No. 63/256,114, filed on Oct. 15, 2021.

(51) Int. Cl.
*A61B 90/98* (2016.01)
*A61B 50/30* (2016.01)

(52) U.S. Cl.
CPC .............. *A61B 90/98* (2016.02); *A61B 50/30* (2016.02)

(58) Field of Classification Search
CPC ......... A61B 90/98; A61B 50/30; H04W 4/35; H04W 4/029; H04L 67/12
See application file for complete search history.

(56) References Cited

U.S. PATENT DOCUMENTS

| | | | |
|---|---|---|---|
| 7,118,029 | B2 | 10/2006 | Nycz et al. |
| 7,362,228 | B2 | 4/2008 | Nycz et al. |

(Continued)

FOREIGN PATENT DOCUMENTS

| | | | |
|---|---|---|---|
| CN | 101976756 | A | 2/2011 |
| WO | 2009003231 | A1 | 1/2009 |

(Continued)

OTHER PUBLICATIONS

International Search Report for Application No. PCT/US2022/046538 dated Dec. 28, 2022, 1 page.

(Continued)

*Primary Examiner* — James J Yang
(74) *Attorney, Agent, or Firm* — Howard & Howard Attorneys PLLC

(57) ABSTRACT

A system for tracking tagged surgical articles across a network. A transport container defining an interior with upper and lower interior surfaces receives a tracking assembly including a, housing supporting an antenna arranged to selectively generate a wave extending helically away from the lower interior surface towards the upper interior surface within the interior. A communication interface wirelessly communicates with a network, and a controller coupled to the housing and disposed in electrical communication with the antenna, and the communication interface is configured to: generate the wave with the antenna to scan the interior of the transport container for tagged surgical articles, receive identity data from each of the tagged surgical articles with the antenna in response to generating the wave, and transmit (Continued)

the identity data, across the network via the communication interface.

17 Claims, 18 Drawing Sheets

(56) References Cited

U.S. PATENT DOCUMENTS

| | | | |
|---|---|---|---|
| 7,518,502 B2 | 4/2009 | Austin et al. | |
| 7,932,826 B2 | 4/2011 | Fritchie et al. | |
| 8,981,938 B2 | 3/2015 | H. Kazerouni | |
| 8,990,099 B2 | 3/2015 | MacDonald et al. | |
| 9,953,197 B2 | 4/2018 | Phillips et al. | |
| 10,109,169 B2 | 10/2018 | Chevalier et al. | |
| 10,368,958 B2 | 8/2019 | Wehrle et al. | |
| 10,390,902 B2 | 8/2019 | Singh et al. | |
| 2007/0257857 A1 | 11/2007 | Marino et al. | |
| 2008/0142605 A1 | 6/2008 | Butsch | |
| 2009/0109033 A1 | 4/2009 | Salvat | |
| 2010/0035539 A1 | 2/2010 | Yoshida et al. | |
| 2011/0315766 A1 | 12/2011 | Phillips et al. | |
| 2014/0082702 A1 | 3/2014 | Supalla | |
| 2015/0153175 A1* | 6/2015 | Skaaksrud | G08B 21/0261 701/23 |
| 2018/0372398 A1 | 12/2018 | Cosgrove et al. | |
| 2019/0303633 A1* | 10/2019 | Pleshek | G06K 7/10366 |
| 2020/0320359 A1 | 10/2020 | Stewart et al. | |
| 2020/0373008 A1 | 11/2020 | Nunes | |

FOREIGN PATENT DOCUMENTS

| | | | |
|---|---|---|---|
| WO | 2014145048 A1 | 9/2014 | |
| WO | WO-2017083715 A1 * | 5/2017 | G06Q 20/208 |

OTHER PUBLICATIONS

English language abstract and machine-assisted English translation for CN 101976756 A extracted from espacenet.com database on Apr. 15, 2024, 9 pages.

* cited by examiner

SYSTEM FOR TRACKING TAGGED SURGICAL ARTICLES WITH A TRANSPORT CONTAINER TRACKING ASSEMBLY

CROSS-REFERENCE TO RELATED APPLICATION

The subject patent application claims priority to and all the benefits of U.S. Provisional Patent Application No. 63/256,114, filed on Oct. 15, 2021, the disclosure of which is hereby incorporated by reference in its entirety.

BACKGROUND

Conventional surgical procedures routinely involve the use of various types of surgical articles, such as tools and associated accessories and/or energy applicators (e.g., bits, burrs, blades, irrigators, lumens, and the like), as well as implants (e.g., anchors, screws, plates, prosthetics, and the like), used to facilitate approaching, treating, and/or stabilizing tissue. Surgical articles maybe reusable (e.g., sterilizable, re-processable, and the like), or may be single-use (e.g., disposable). Many types of surgical articles are packaged in sealed containers, realized such as by sealed or otherwise sterile enclosures which, in turn, may be disposed within a box. Here, boxes may contain one or more surgical articles of a specific size, type, and/or configuration, or ranges thereof, the details of which may be printed or otherwise presented on one or more labels and/or tags secured to the box.

Depending on the type of surgical procedure being performed, various sizes and/or types of surgical articles may be required. A logistics representative responsible for sourcing surgical articles generally provides medical facilities with surgical articles as they are needed. Here, the logistics representative may maintain a working inventory of surgical articles ready to be provided to the medical facility. To this end, the working inventory may be realized as a plurality of surgical articles stored in one or more transport containers. A single transport container may contain an assortment of different surgical articles organized or otherwise defined by common sizes, types, and the like, which may be optimized to suit a particular medical facility's needs, or may be based on a particular category or type of procedure carried out at the medical facility (e.g., specific orthopedic procedures, trauma procedures, and the like). If a medical facility where the surgical procedure is being performed needs a specific surgical article for a given procedure, the logistics representative will generally source the surgical article from the working inventory.

If the working inventory is running low on (or is out of) a particular surgical article, the logistics representative may need to replenish or otherwise supplement the working inventory. To this end, specific surgical articles may be separately sourced by the logistics representative when needed (e.g., via overnight shipping from a warehouse). In addition, transport containers may be exchanged and subsequently replenished with new surgical articles, such as at a warehouse or another facility. In such a scenario, the transport container may be inventoried, such as by scanning or otherwise inspecting its contents, to determine which new and/or replacement surgical articles are needed in order to replenish the transport container.

Depending on the size and quantity of transport containers a logistics representative is responsible for, as well as the size, shape, configuration, and assortment of surgical articles placed therein, it can be difficult to readily ascertain when the transport container needs to replenished or supplemented, in particular where the logistics representative frequently accesses and rearranges surgical articles in transport containers. Here, the logistics representative may inventory the contents of the transport container (e.g., by scanning or manually inspecting surgical articles as they are removed), and may carefully track inventory of the transport containers. However, this process can be cumbersome and time consuming, and it will be appreciated that it can be difficult to readily confirm availability of the surgical articles when a specific quantity of surgical articles is needed on short notice.

Accordingly, there remains a need in the art to overcome one or more of the challenges described above.

SUMMARY

A system for tracking tagged surgical articles across a network includes a transport container and a tracking assembly. The transport container defines an interior having a lower interior surface, an upper interior surface, and a plurality of interior side walls extending between the lower interior surface and the upper interior surface. The tracking assembly includes a housing shaped to be received within the interior of the transport container. The tracking assembly also includes an antenna supported by the housing adjacent to the lower interior surface and being arranged to selectively generate a wave extending helically away from the lower interior surface and towards the upper interior surface within the interior of the transport container. The tracking assembly further includes a communication interface for wirelessly communication with the network. The tracking assembly further includes a controller coupled to the housing and disposed in electrical communication with the antenna and the communication interface.

The controller is being configured to generate the wave with the antenna to scan the interior of the transport container for tagged surgical articles, receive identity data from each of the tagged surgical articles with the antenna in response to generating the wave, and transmit the identity data across the network via the communication interface.

The system for tracking tagged surgical articles across the network permits a logistics representative to quickly inventory the surgical articles in the transport container, thus permitting the logistics representative to readily ascertain when the transport container runs low on (or out of) a particular surgical article and thus when the transport container needs to be replenished or supplemented, in particular where the logistics representative frequently accesses and rearranges the surgical articles. The system for tracking tagged surgical articles across the network also permits the logistics representative to quickly source surgical articles for medical facilities as they are needed.

DETAILED DESCRIPTION

Figure 1:
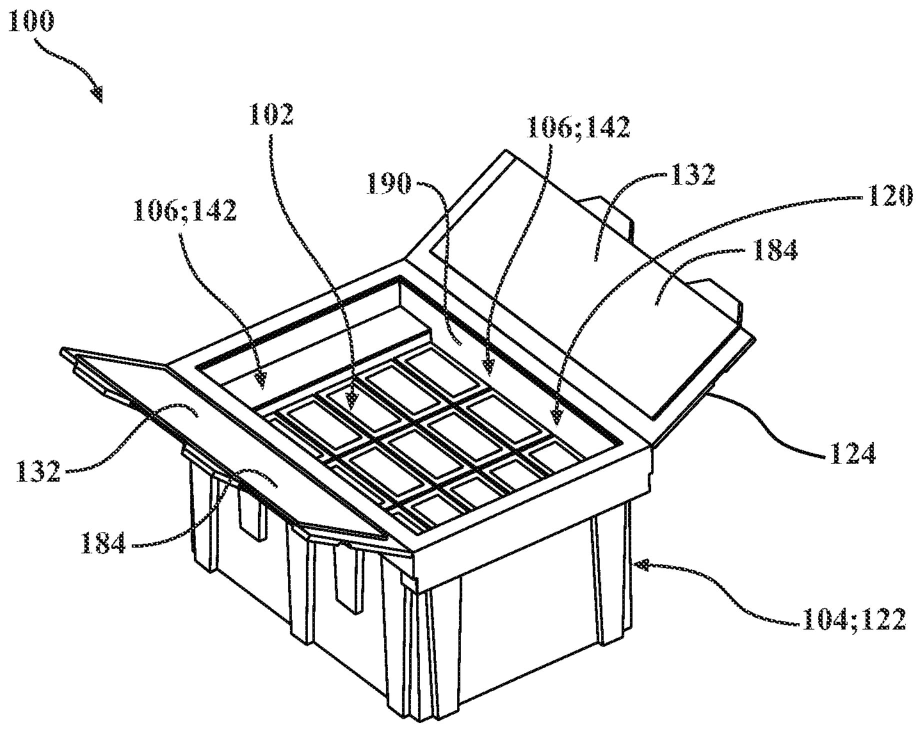
FIG. 1 is a perspective view depicting portions of a system for tracking tagged surgical articles, shown with a transport container defining an interior in which a plurality of tagged surgical articles are disposed adjacent to a tracking assembly according to aspects of the present disclosure.
Figure 2:
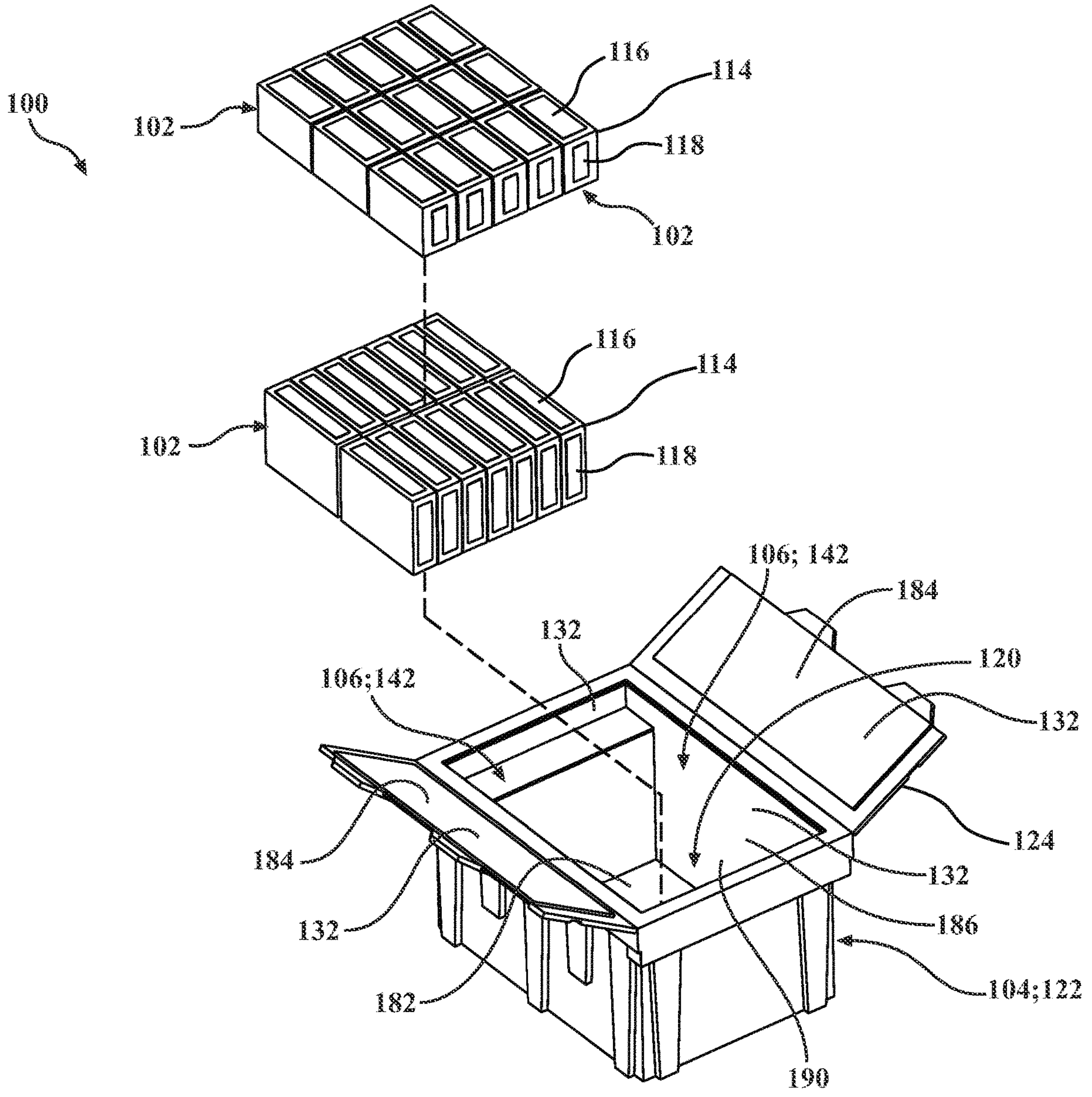
FIG. 2 is a partially-exploded perspective view of the portions of the system of FIG. 1, shown with the plurality of tagged surgical articles spaced from the interior of the transport container, with the tracking assembly shown having a housing with a base and a tower, and shown having a shield having interior shield walls disposed about the tower.
Figure 3:
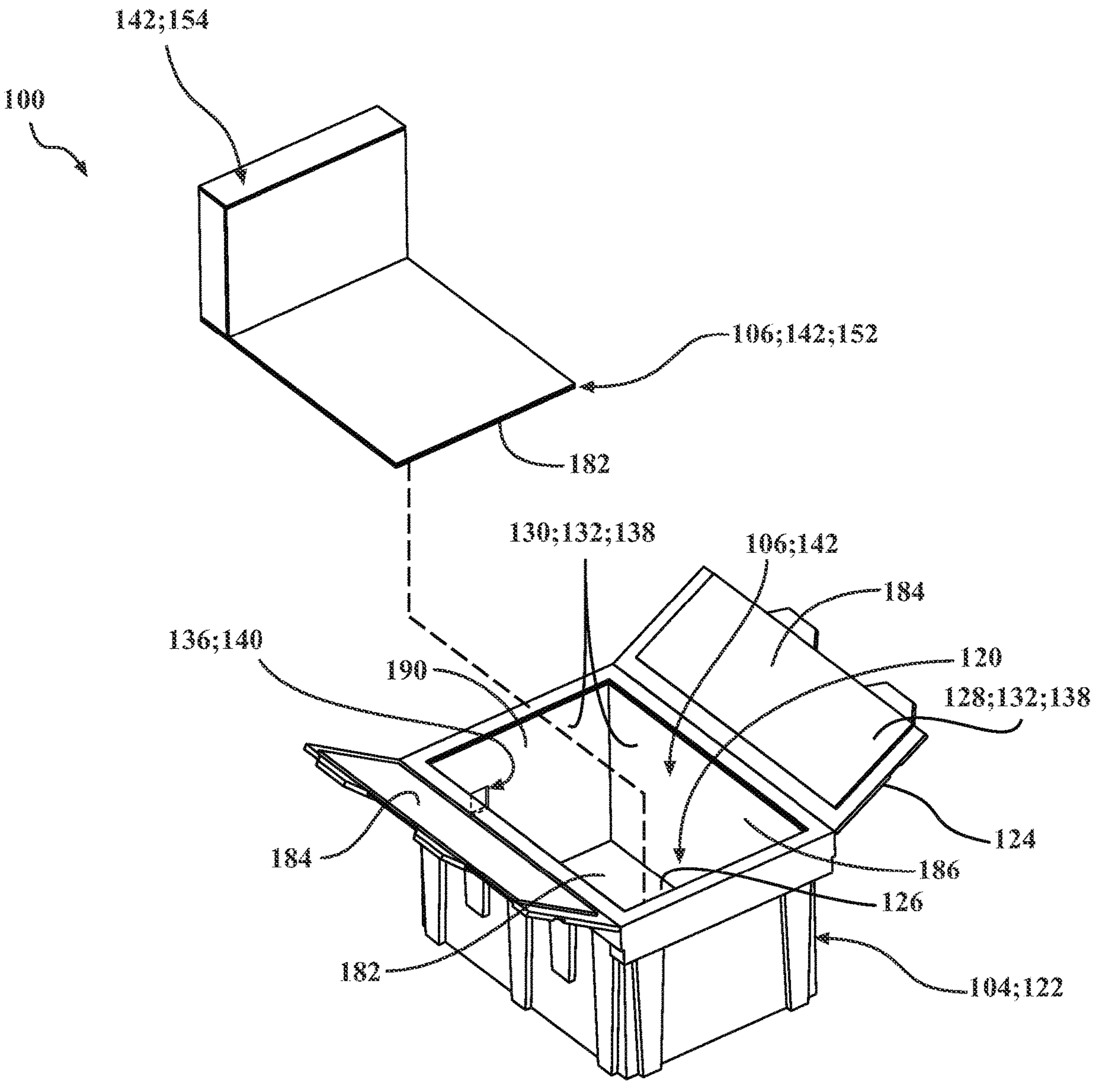
FIG. 3 is another partially-exploded perspective view of portions of the system of FIGS. 1-2, shown with the tracking assembly spaced from the interior of the transport container.
Figure 4:
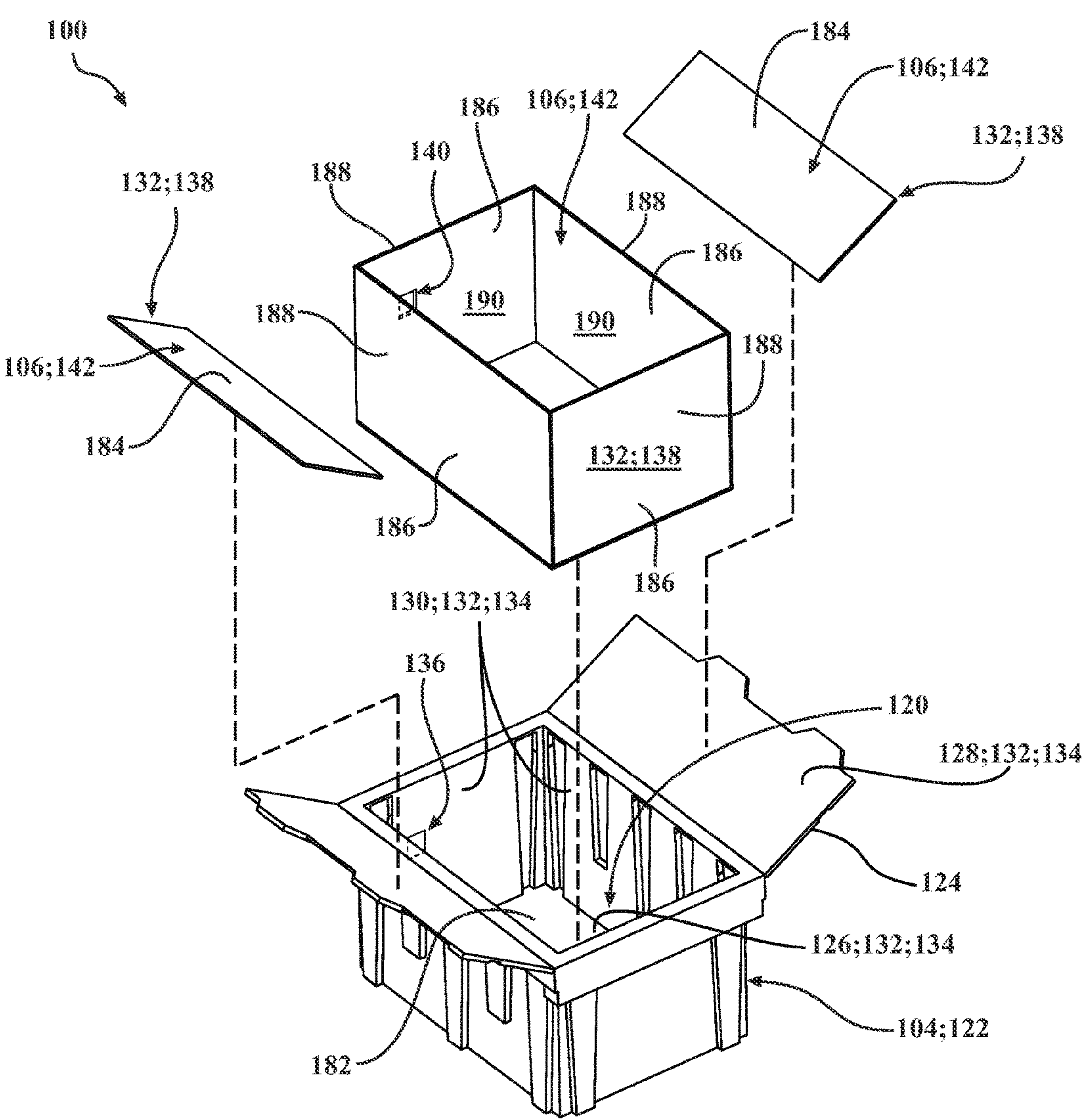
FIG. 4 is another partially-exploded perspective view of portions of the system of FIGS. 1-3, shown with the shield spaced from the interior of the transport container.
Figure 5A:
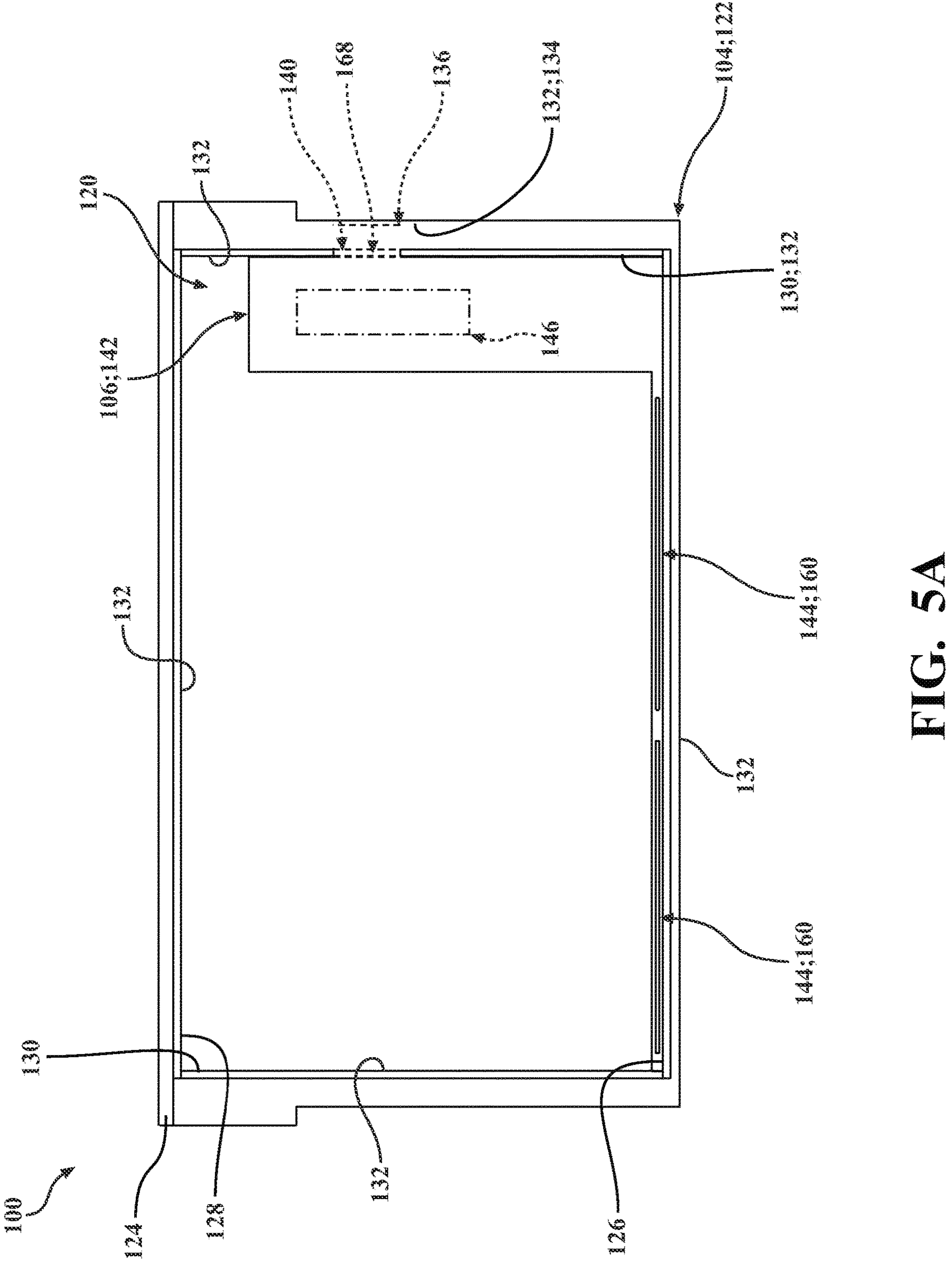
FIG. 5A is a right-side schematic view of the transport container and the tracking assembly of the system of FIGS. 1-4, shown with the tracking assembly disposed in the interior of the transport container.
Figure 5B:
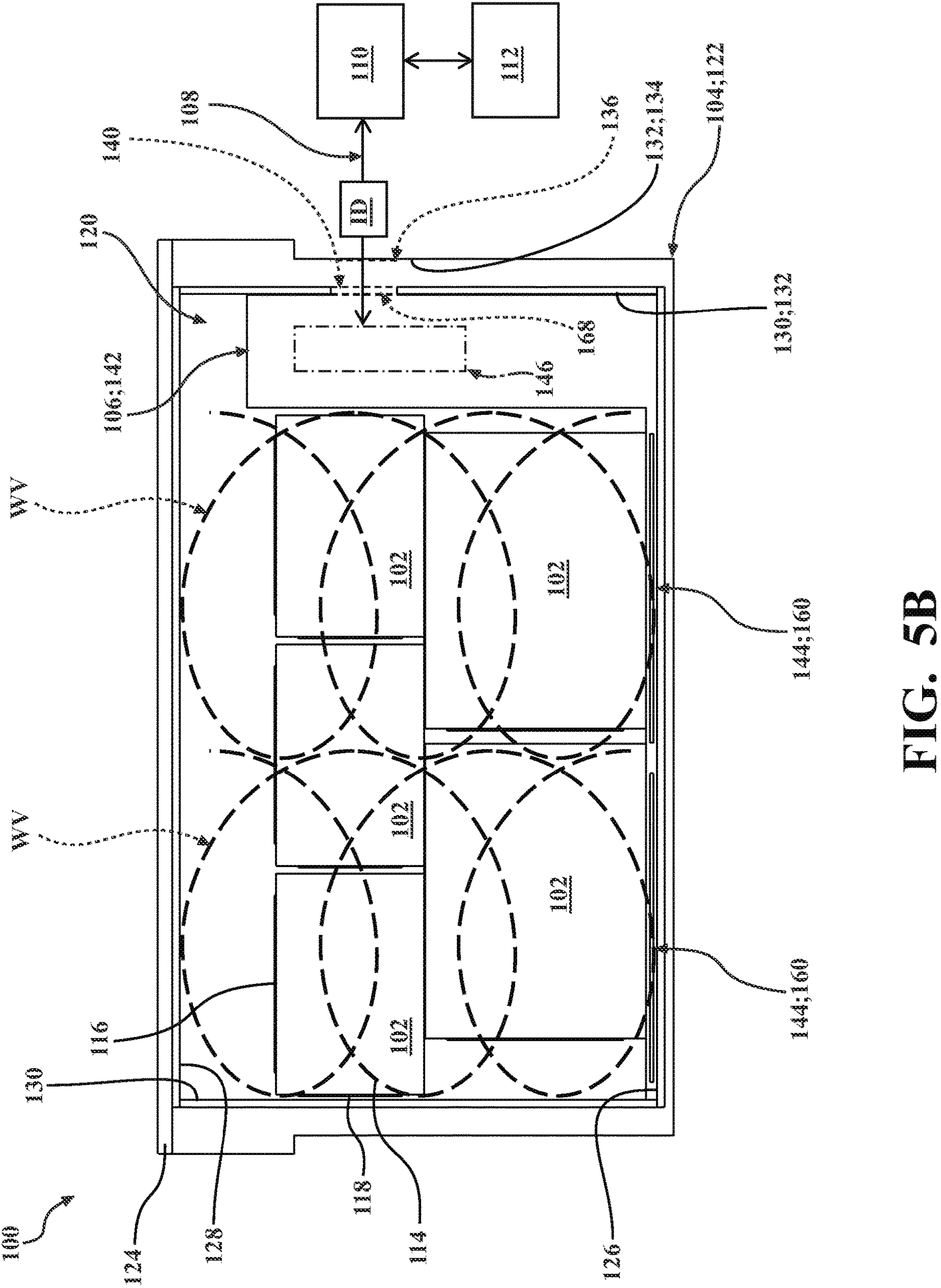
FIG. 5B is another right-side schematic view of the transport container and the tracking assembly of FIG. 5A, shown with the plurality of tagged surgical articles disposed in the interior of the transport container.
Figure 5C:
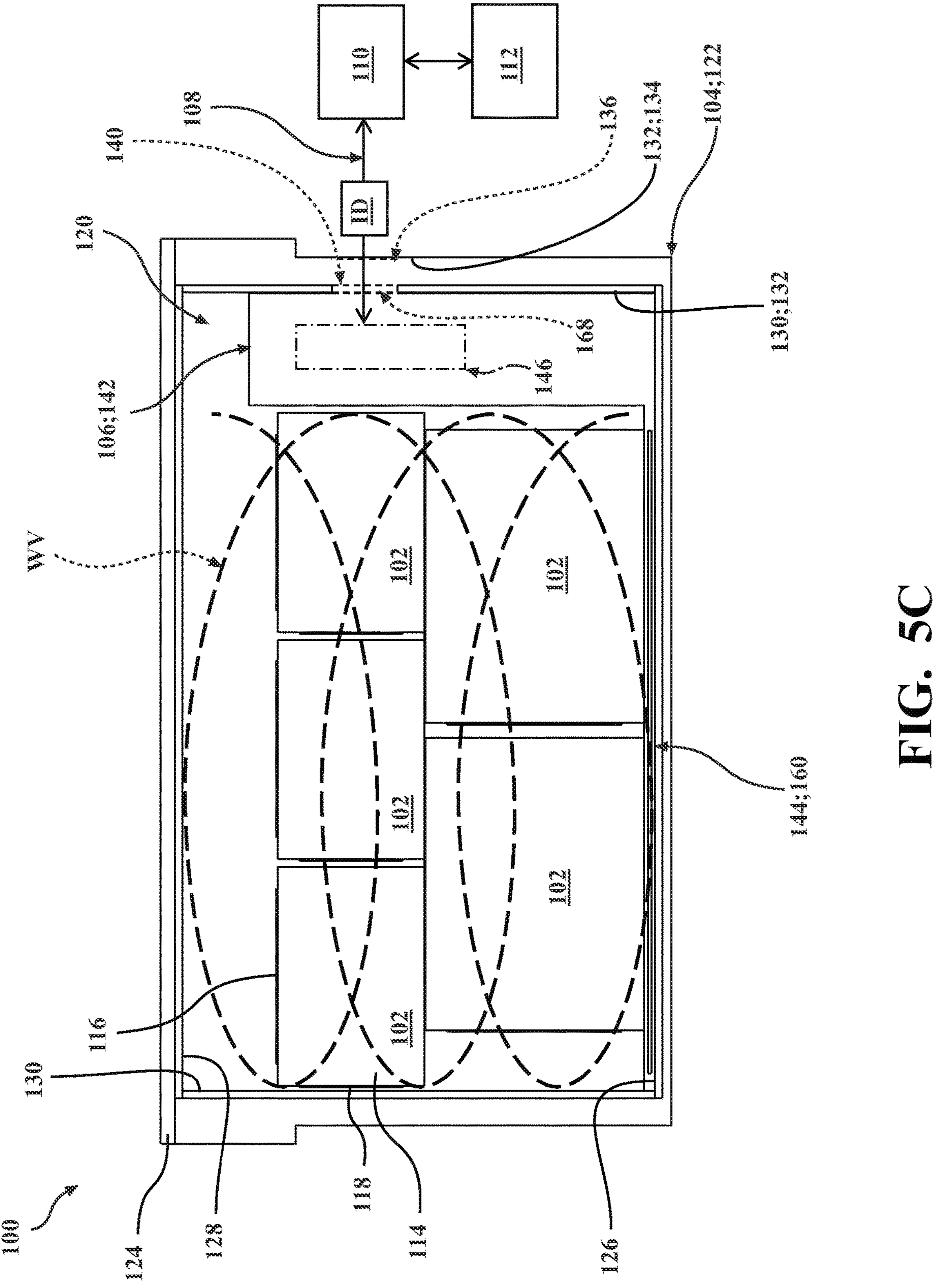
FIG. 5C is a right-side schematic view of another version of the transport container and the tracking assembly of FIG. 5B.

Referring now to FIGS. 1-5B, a system 100 is generally shown for tracking a plurality of tagged surgical articles 102 (hereinafter, "surgical articles 102") placed in a transport container 104 via a tracking assembly 106. As is described in greater detail below, the tracking assembly is configured to communicate across a network 108 with a server 110 disposed in communication with various remote electronic devices 112 in order to facilitate tracking surgical articles 102 disposed in the transport container 104.

In the representative versions illustrated throughout the drawings, the surgical articles 102 are generically depicted as generally rectangular boxes 114 to which respective labels 116 and tags 118 are affixed in order to, among other things, identify the surgical article 102 inside the box 114. The surgical articles 102 are generally configured for utilization during various types of medical and/or surgical procedures, and may be of numerous types, styles, and/or configurations. While not illustrated in detail herein, surgical articles 102 may be realized as tools, components, or materials utilized in the treatment of tissue, or may be realized as implantable components, prosthetics, and the like. Surgical articles 102 may be packaged individually in a single box 114, or a single box 114 may include a plurality of surgical articles 102 of the same type, size, configuration, and the like. It is also contemplated that a single box 114 may include a plurality of surgical articles 102 of different types, sizes, configurations, and the like. The surgical articles 102 may be placed in sterile enclosures, packages, and the like (not shown, but generally known in the related art) which, in turn, are placed in boxes 114. Alternatively, the box 114 itself may be realized as a sterile enclosure to which the label 116 and the tag 118 are affixed. Similarly, the surgical article 102 may itself be provided with the label 116 and/or tag 118.

While a number of different configurations of boxes 114 are contemplated by the present disclosure, in some versions, certain boxes 114 may be approximately 5"×3"×1" (inches), 6"×6"×3" (inches), 6"×6"×1.4" (inches), 6"×12"×3" (inches). Furthermore, while the boxes 114 are depicted generically throughout the drawings, it will be appreciated that the system 100 can detect surgical articles 102 of various types, styles, and configurations via the use of tags 118 as described in greater detail below, with or without utilizing the box 114, and/or with different types or styles of enclosures, packaging, and the like other than boxes 114. Other configurations are contemplated.

The labels 116 are placed on a top surface of the boxes 114 to, among other things, identify the respective surgical article 102. Here, labels 116 may include text, symbols, bar codes, and the like, arranged in various ways to facilitate managing inventory, distribution, sorting, handling, identification, and the like. The tags 118 are placed on a side surface of the box to facilitate identification of the respective surgical article 102. The tags 118 are realized as Radio Frequency Identification RFID tags operable according to Ultra High Frequency UHF RFID protocols, and may include or otherwise define identity data ID corresponding to the surgical article 102. Identity data ID may include part numbers, lot numbers, serial numbers, date information, processing information, codes (e.g., an Electronic Product Code EPC), and the like. Other configurations are contemplated.

The transport container 104 defines an interior 120 into which the tracking assembly 106 and one or more surgical articles 102 are disposed, as described in greater detail below. In the representative version illustrated herein, the transport container 104 is realized as a plastic tote 122 to which interlocking flaps 124 are pivotably coupled. More specifically, the upper interior surface 128 of the transport container 104 may include interlocking flaps 124 pivotably coupled to a plurality of interior side walls 130. However, it will be appreciated that the transport container 104 could be configured in other ways. The interior 120 of the transport container 104 defines a lower interior surface 126, an upper interior surface 128, and the plurality of interior side walls 130 extending between the lower interior surface 126 and the upper interior surface 128 (see FIG. 4). Here, the upper interior surface 128 is defined by the flaps 124 when in a closed configuration (see FIGS. 5A-5B). In one aspect, the transport container 104 is provided with shield 132 which, as described in greater detail below, is configured facilitate proper operation and consistent, high level accuracy of the tracking assembly 106. To this end, in some versions, the lower interior surface 126, the upper interior surface 128, and the interior side walls 130 of the transport container 104, as well as portions of the tracking assembly 106, may be provided with a coating 134 such as CuPro Cote™ copper-based paint. Other configurations are contemplated. In some versions, additional layers of different types of coating 134 may be provided, such as a polyurethane paint applied over CuPro Cote™ copper-based paint to help ensure durability. As shown in FIGS. 3-5C, the coating 134 is not applied along an area of one of the interior side walls 130 in order to define a shield window 136 arranged relative to components of the transport container 104 to facilitate communication across the network 108 as described in greater detail below. More specifically, the shield window 136 defined by the shield 132 may be arranged relative to the communication interface 146 to facilitate transmittal of the identity data ID across the network 108 via the communication interface 146. In some versions, the shield 132 may include additional components and/or materials. For example, the shield 132 may include a liner 138 disposed along the lower interior surface 126, the upper interior surface 128, and the interior side walls 130 of the transport container 104, as well as on portions of the tracking assembly 106. Here, the liner 138 may be constructed from or otherwise realized by one or more pieces of metallic foil panels and/or tape secured together and to the coating 134 (e.g., via foam, adhesive, and the like) or otherwise supported within the interior 120 of the transport container 104. Here too as shown in FIGS. 3-5C, a liner window 140 is defined so as to be positioned adjacent to and in alignment with the shield window 136 to facilitate communication of the tracking assembly 106 across the network 108.

Referring now, generally, to FIGS. 1-16, as noted above, the tracking assembly 106 of the system 100 is configured to identify surgical articles 102 disposed within the interior 120 of the transport container 104 and communicate across the network 108 to, among other things, transmit identity data ID of identified surgical articles 102 to the server 110 for access by various remote electronic devices 112 as described in greater detail below. To this end, the tracking assembly 106 generally includes a housing 142, an antenna 144, a communication interface 146, a controller 148, and at least one battery module 150. The housing 142 is shaped to be received within the interior 120 of the transport container 104. The antenna 144 is supported by the housing 142 adjacent to the lower interior surface 126 and is arranged to selectively generate a wave WV extending helically away from the lower interior surface 128 and towards the upper interior surface 128 within the interior of the transport container 104 (see FIG. 5B). It is to be appreciated that the antenna 144 may be configured to generate the wave WV in a helical configuration. The communication interface 146 is provided for wirelessly communicating with the network 108. The battery module 150 is configured to power the controller 148, and may be operatively attached to the tower 154 and supported in the tower interior 120.

The controller 148 is powered by the battery module 150, is coupled to the housing 142, and is disposed in electrical communication with the antenna 144 and the communication interface 146. The controller 148 may be supported by the housing 142. The controller 148 is configured to, among other things, generate the wave WV with the antenna 144 to scan the interior 120 of the transport container 104 for tagged surgical articles 102, receive identity data ID from each of the tagged surgical articles 102 with the antenna 144 in response to generating the wave WV, and transmit the identity data ID across the network 108 via the communication interface 146. More specifically, the controller 148 is configured to, among other things, generate the wave WV with the antenna 144 to scan the interior 120 of the transport container 104 for the tags 118 of surgical articles 102, receive identity data ID from each of the tags 118 of the respective surgical articles 102 in response to generating the wave WV, and transmit the identity data ID to the server 110 (and/or one or more remote electronic devices 112) across the network 108 via the communication interface 146. Each of the components introduced above will be described in greater detail below.

The system 100 for tracking tagged surgical articles 102 across the network 108 permits a logistics representative to quickly inventory the tagged surgical articles 102 in the transport container 104, thus permitting the logistics representative to readily ascertain when the transport container 104 runs low on (or out of) a particular surgical article 102 and thus when the transport container 104 needs to be replenished or supplemented, in particular where the logistics representative frequently accesses and rearranges the tagged surgical articles 102. The system 100 for tracking tagged surgical articles 102 across the network 108 also permits the logistics representative to quickly source surgical articles 102 for medical facilities as they are needed.

As shown in FIGS. 1-5C and, the tracking assembly 106 may further include a shield 132 arranged to block waves WV generated by the antenna 144 from exiting the transport container 104. The shield 132 of the tracking assembly 106 may be used instead of, or in addition to, the shield 132 of the transport container 104. Moreover, the shield 132 of the tracking assembly 106 may include any of the characteristics of the shield 132 of the transport container 104 as described herein. The shield 132 of the tracking assembly 106 will be described in further detail below.

Figure 6:
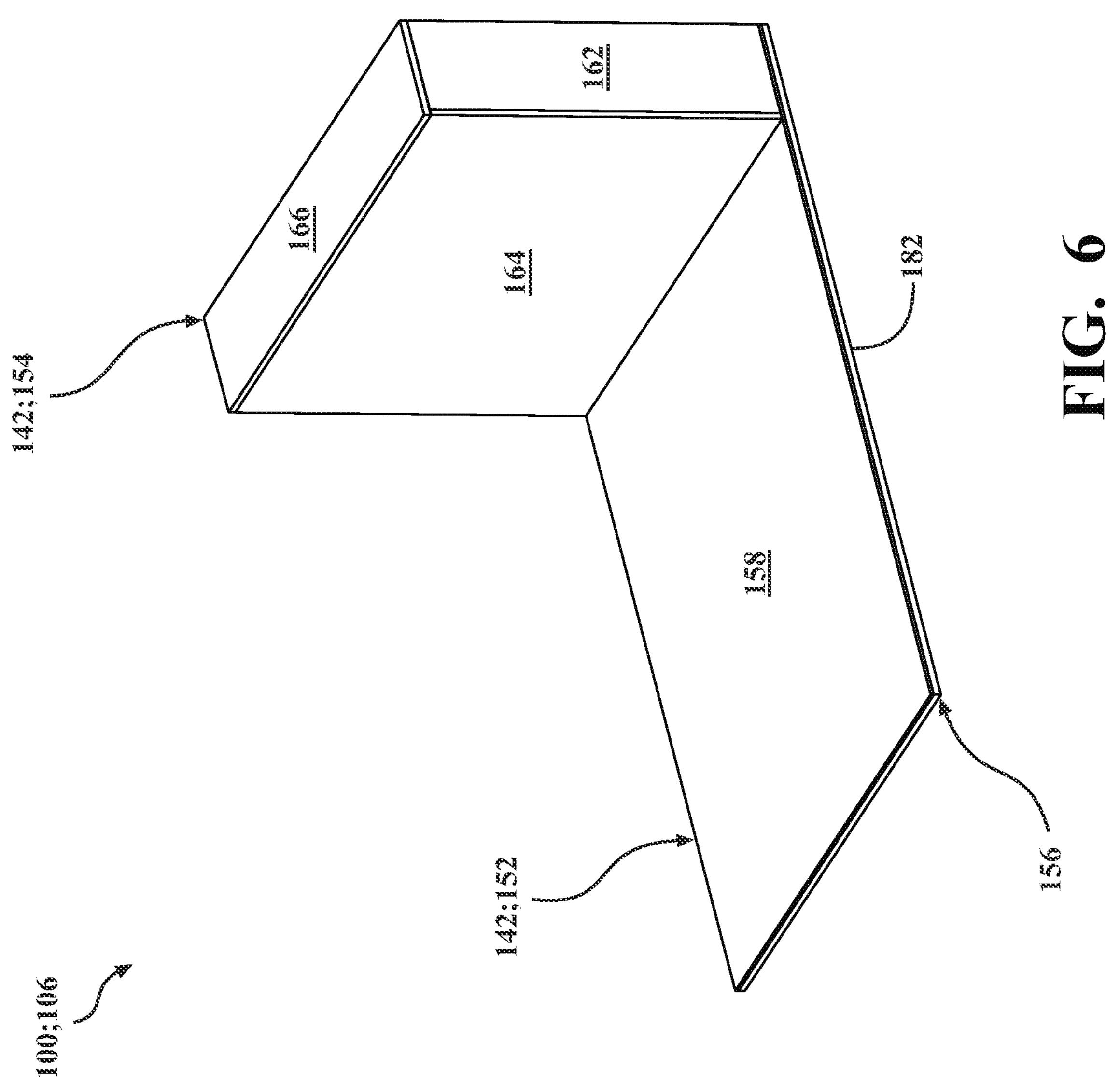
FIG. 6 is an enlarged perspective view of the tracking assembly of the system of FIGS. 1-5B, shown having the housing with the base and the tower.
Figure 7:
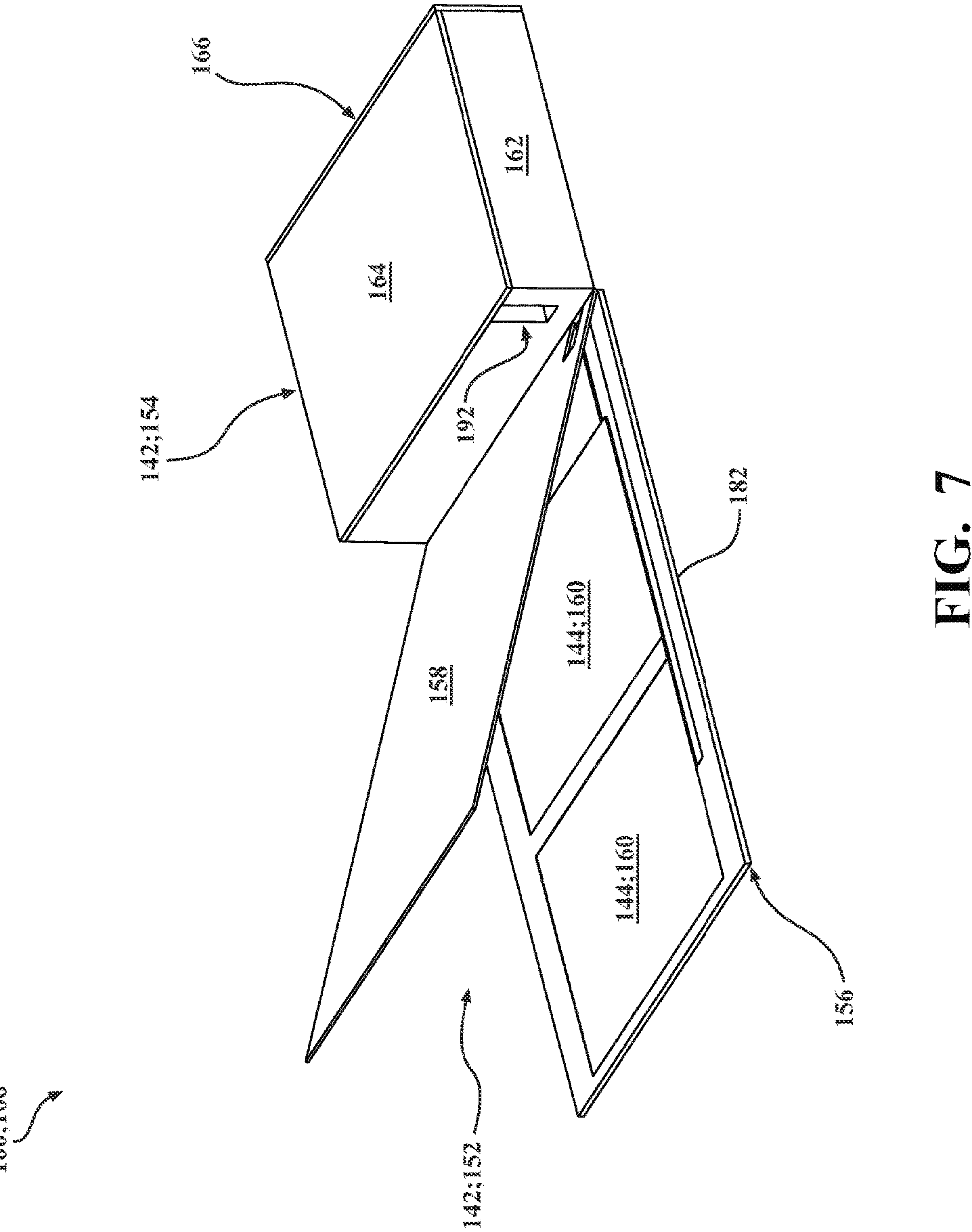
FIG. 7 is another enlarged perspective view of the tracking assembly of the system of FIGS. 1-6, shown with the base having a base frame supporting antennas and having a base cover articulated relative to the base frame, and shown with the tower articulated relative to the base.

Referring now to FIGS. 6-10, the housing 142 of the tracking assembly 106 generally includes a base 152 and a tower 154. In one aspect the tower 154 is pivotably coupled to the base 152 of the housing 142. The base 152 of the housing 142 may be adjacent to the lower interior surface 126 of the transport container 104. The base 152 may have a generally rectangular profile sized similarly to the lower interior surface 126 and may include a base frame 156 and a base cover 158 coupled to the base frame 156. In some aspects, as shown in FIGS. 6 and 7, the base cover 158 is pivotably covered to the base frame 156. In other aspects, as shown in FIGS. 12-15, the base cover 158 is slidably coupled to the base frame 156. The base frame 156 supports the antenna 144 therein, which is realized by two generally rectangular antenna modules 160 as described in greater detail below.

The base cover 158 may be selectively moveable relative to the base frame 156 to permit access to the antenna 144. To this end, the housing 142 may define a slot 180 sized to permit the base cover 158 to selectively move relative to the base frame 156 to permit access to the antenna 144. Channels, notches, and the like (not shown in detail) may be defined in the base 152 for routing wires 194 between the antenna module 160 and the controller 148. It will be appreciated that shield 132 is not provided on the base cover 158, but may be provided on portions of the tower 154. More specifically, the shield may be disposed in spaced relation from the base cover 158 to permit waves generated with the antenna 144 to scan the interior 120 of the transport container 104 for tagged surgical articles 102, and the shield 132 may be adjacent to the base frame 156 and the tower 154 to prevent waves generated with the antenna 144 from exiting the transport container 104 through the base frame 156 and/or the tower 154, which could interfere with adjacent transport containers 104.

The shield 132 may be integral with the housing 142, including but not limited to formed integrally with the housing 142. Alternatively, the shield 132 may be a separate component than the housing 142. The shield 132 may even be formed as a separate component than the housing 142, and later joined with the housing 142 to become integral. In non-limiting examples, the shield 132 may be mechanically affixed, including but not limited to stapled or crimped, to the housing 142 to become integral with the housing 142, and/or the shield 132 may be taped, glued, or otherwise adhered to the housing 142 to become integral with the housing 142.

The shield 132 may include at least one chosen from a lower shield surface 182 arranged to block waves WV generated by the antenna 144 from exiting the lower interior surface 126 of the transport container 104, an upper shield surface 184 arranged to block waves WV generated by the antenna 144 from exiting the upper interior surface 128 of the transport container 104, and interior shield walls 186 arranged to block waves WV generated by the antenna 144 from exiting the interior side walls 130 of the transport container 104. In other words, the shield 132 may include any combination of the lower shield surface 182, the upper shield surface 184, and the interior shield walls 186, including but not limited to all of the lower shield surface 182, the upper shield surface 184, and the interior shield walls 186. In one aspect, as shown in FIGS. 1-5C, the shield 132 includes the interior shield walls 186, and the interior shield walls 186 are disposed about the tower 154. In another aspect, as shown in FIGS. 12-15, the shield 132 includes the interior shield walls 186, and the tower 154 is disposed exterior to the interior shield walls 186.

Moreover, the housing 142 includes exterior surfaces 188 facing the transport container 104 and interior surfaces 190 defining a housing interior 120. In one aspect, the shield 132 is disposed on the exterior surfaces 188 of the housing 142. In another aspect, the shield 132 is disposed on the interior surfaces 190 of the housing 142. It is to be appreciated that the shield 132 may be constructed from or otherwise realized by one or more pieces of metallic foil panels and/or tape secured together. The metallic foil panels and/or tape may be disposed on the exterior surfaces 188 of the housing 142, may be disposed on the interior surfaces 190 of the housing 142, or may be disposed on both the exterior surfaces 188 of the housing 142 and on the interior surfaces 190 of the housing 142.

Figure 8:
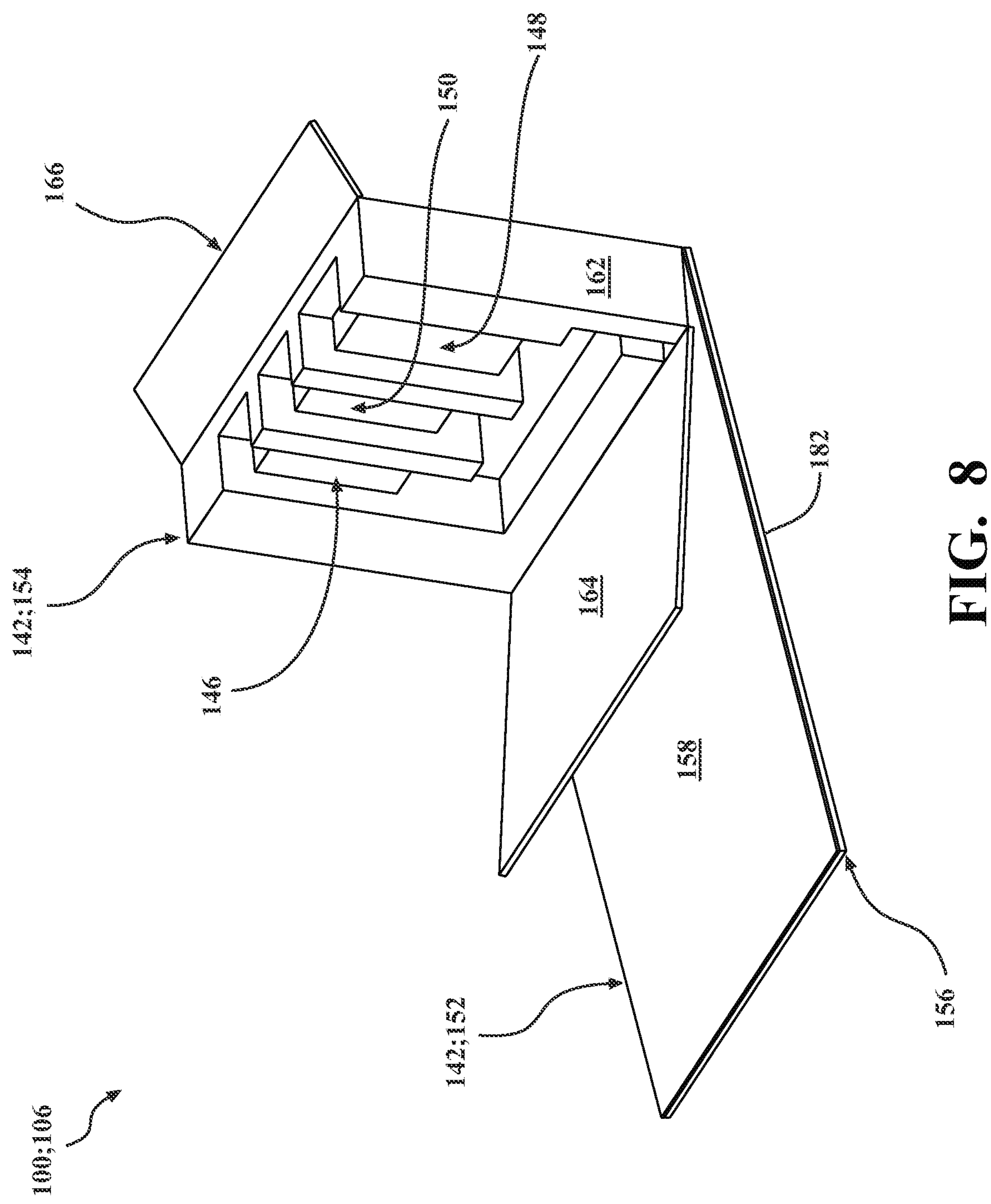
FIG. 8 is another enlarged perspective view of the tracking assembly of the system of FIGS. 1-7, shown with the tower articulated relative to the base and having a tower frame supporting a controller, a battery module, and a communication interface, and shown with the tower having a tower cover and a tower lid each articulated relative to the tower frame.

The tower 154 generally may include a tower frame 162, a tower cover 164 pivotably coupled to the tower frame 162, and a tower lid 166 pivotably coupled to the tower frame 162. The tower 154 may be coupled to the base 152 and extend away from the lower interior surface 126 of the transport container 104. The tower 154 may define a tower interior 120, and the communication interface 146 and the controller 148 may be operatively attached to the tower 154 and supported in the tower interior 120. As is best shown in FIG. 8, the tower frame 162 is shaped to accommodate the communication interface 146, the controller 148, and the battery module 150 therein, and may be provided with various channels, notches, and the like (not shown in detail) to facilitate routing wires 194 between components of the tracking assembly 106. More specifically, the tower 154 may define a channel 192 to facilitate routing of wires 194 between at least one chosen from the communication interface 146, the controller 148, and the battery module 150 to the antenna 144. In other words, the channel 192 may facilitate routing of wires 194 between any combination of the communication interface 146, the controller 148, and the battery module 150, including but not limited to all of the communication interface 146, the controller 148, and the battery module 150, to the antenna 144.

Figure 9:
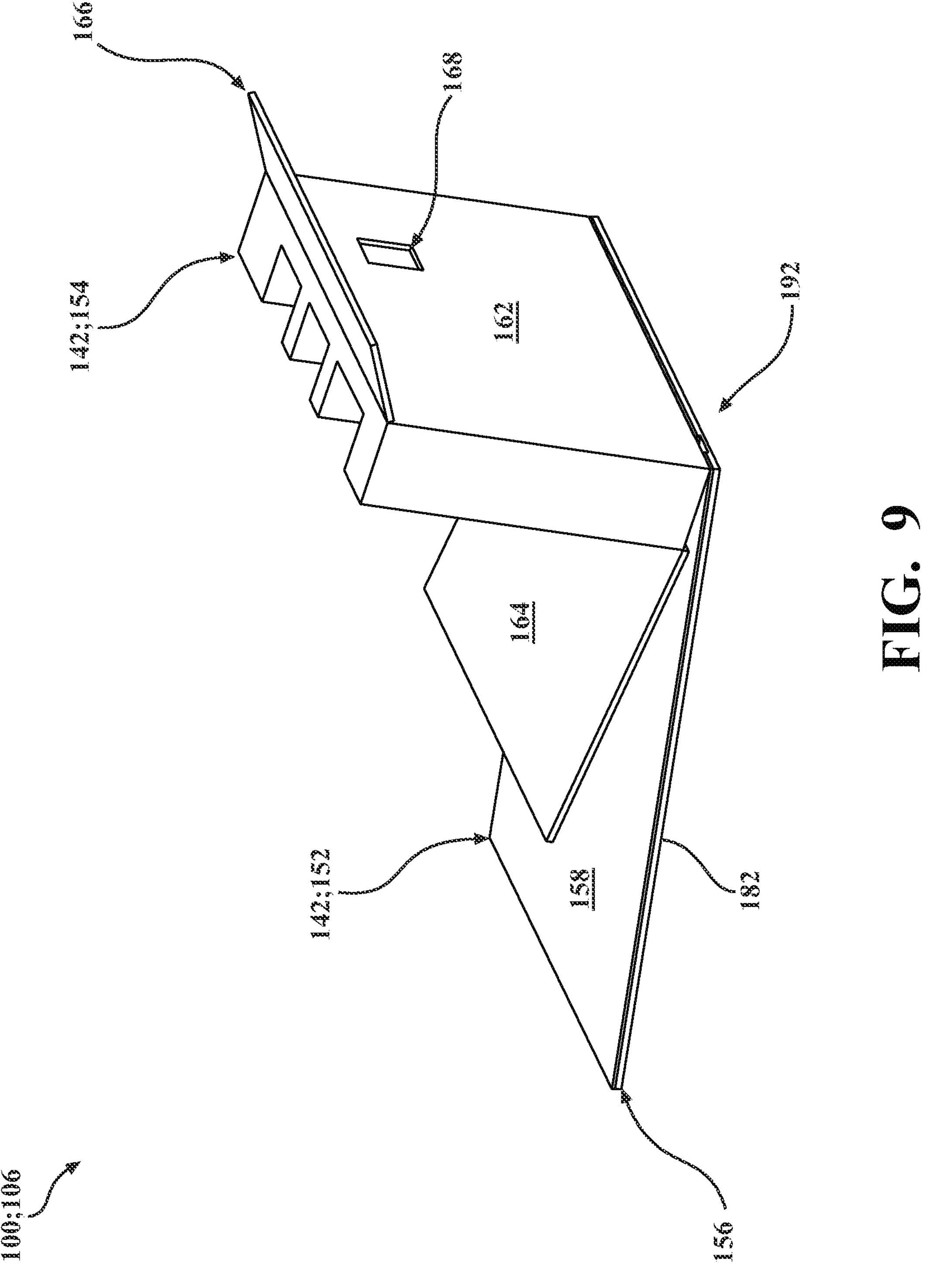
FIG. 9 is another enlarged perspective view of the portions of the tracking assembly of FIG. 8.
Figure 10:
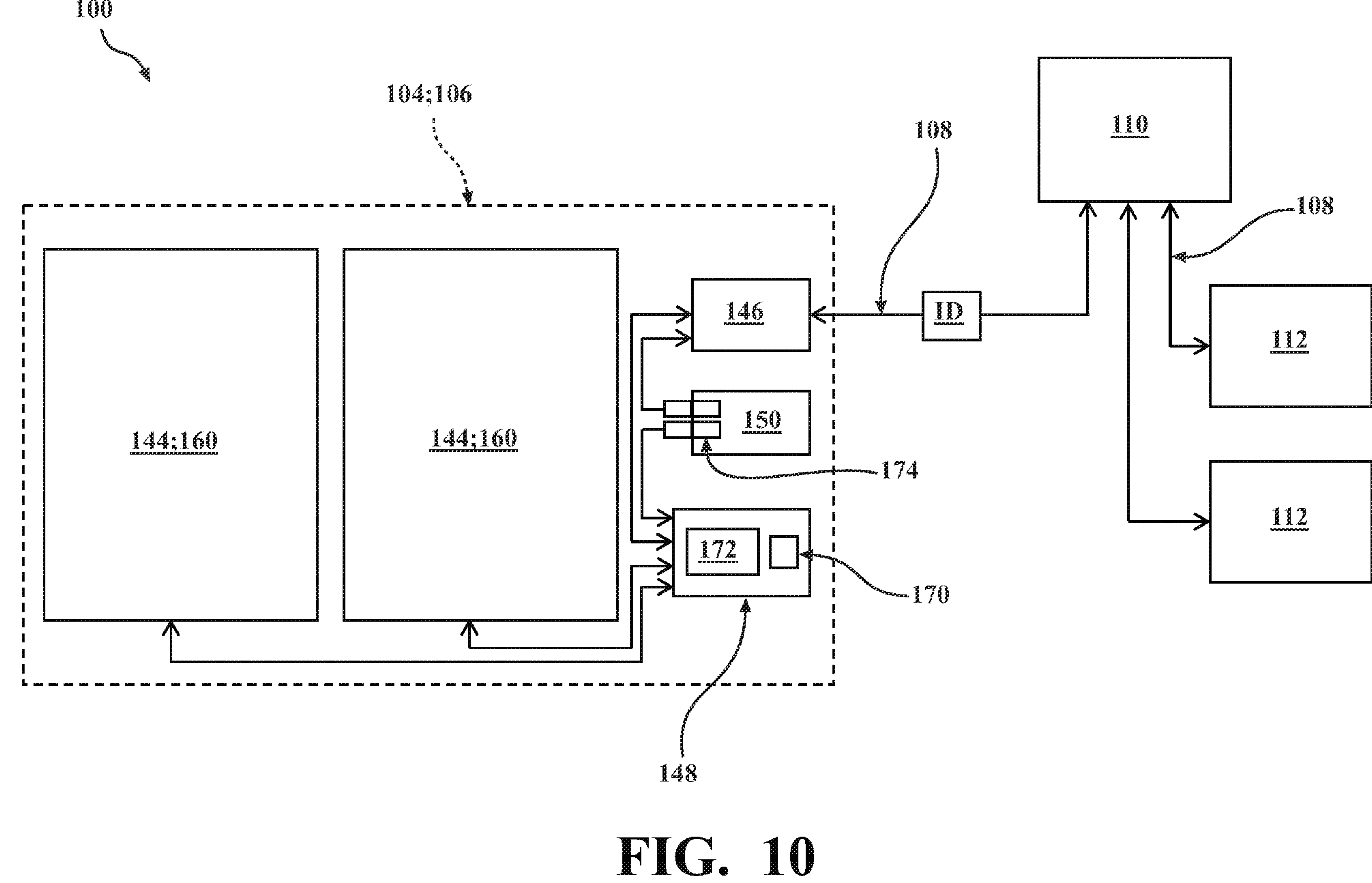
FIG. 10 is a schematic representation of portions of the system of FIGS. 1-9, shown with the communication interface disposed in electrical communication with a server across a network.
Figure 11:
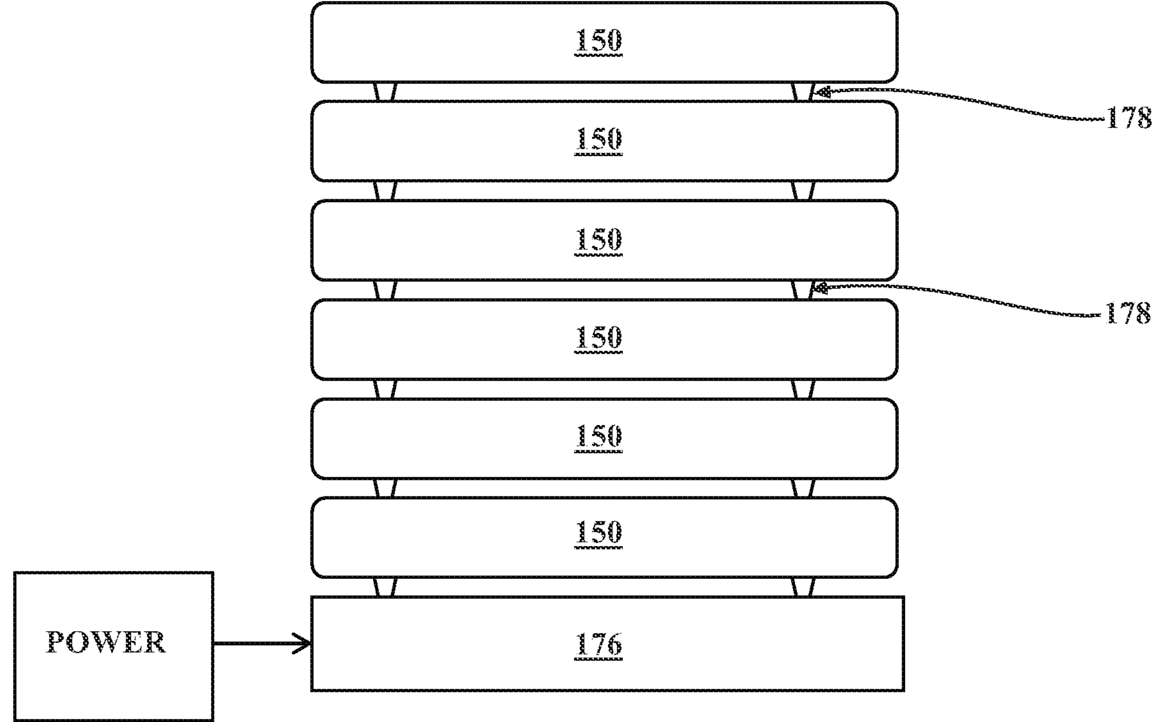
FIG. 11 is a schematic representation of a charging station for the battery module of the system of FIGS. 1-10.
Figure 12:
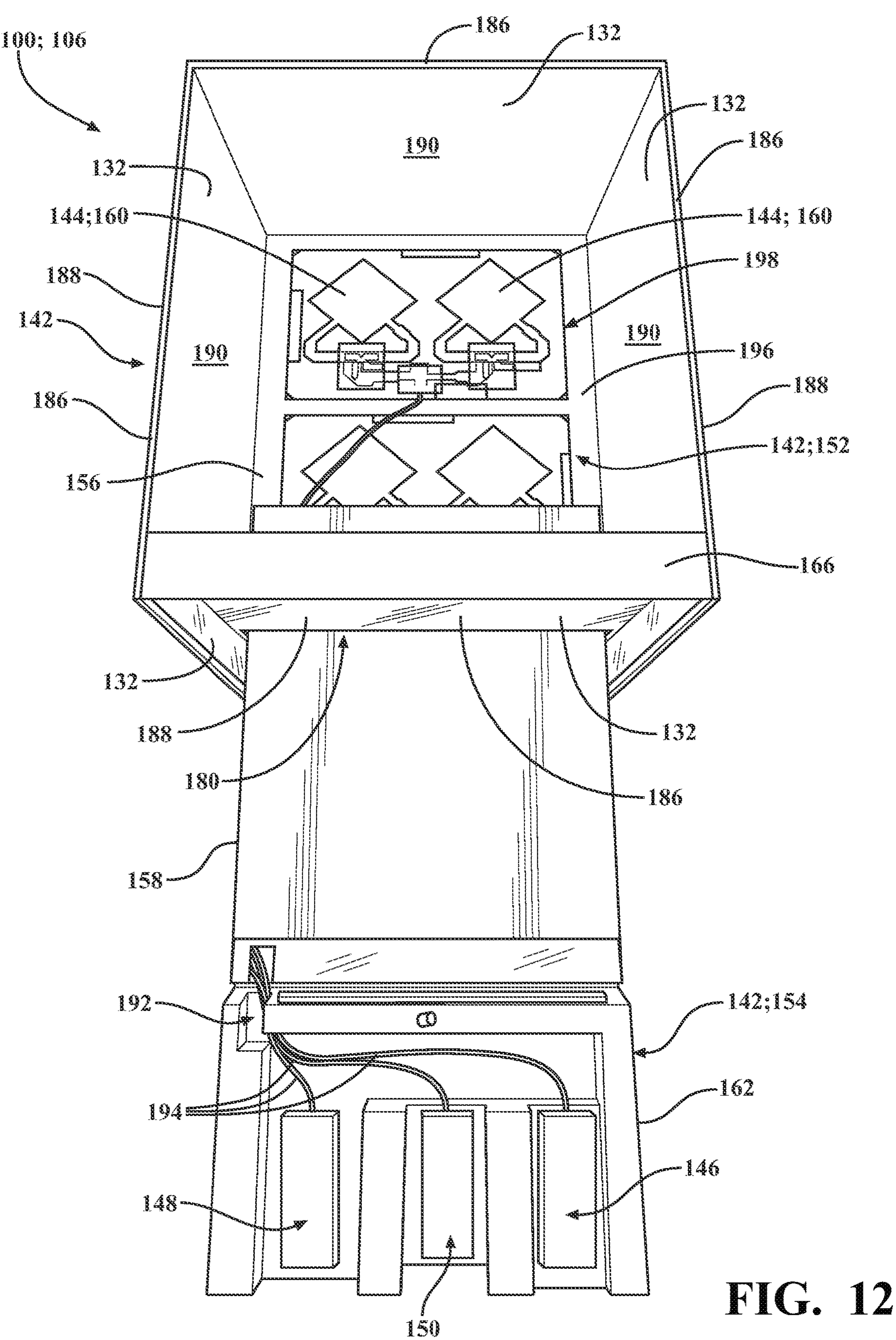
FIG. 12 is a perspective view of another aspect of the tracking assembly, shown with the base having the base frame supporting the antenna and having a base cover coupled to the base frame and selectively moveable relative to the base frame to permit access to the antenna.
Figure 13:
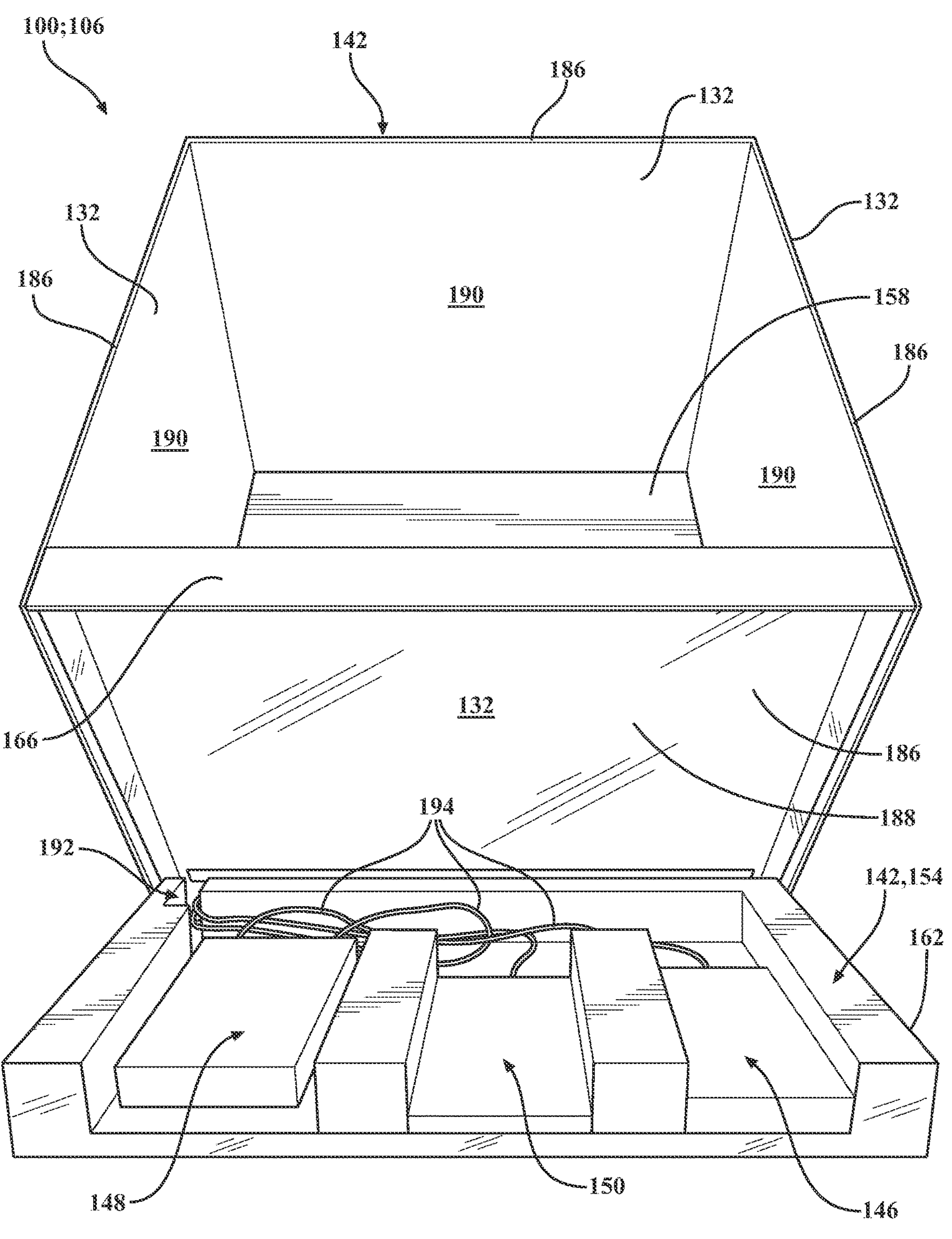
FIG. 13 is a perspective view of the tracking assembly of FIG. 12, with the tower pivotably coupled to the base cover.
Figure 14:
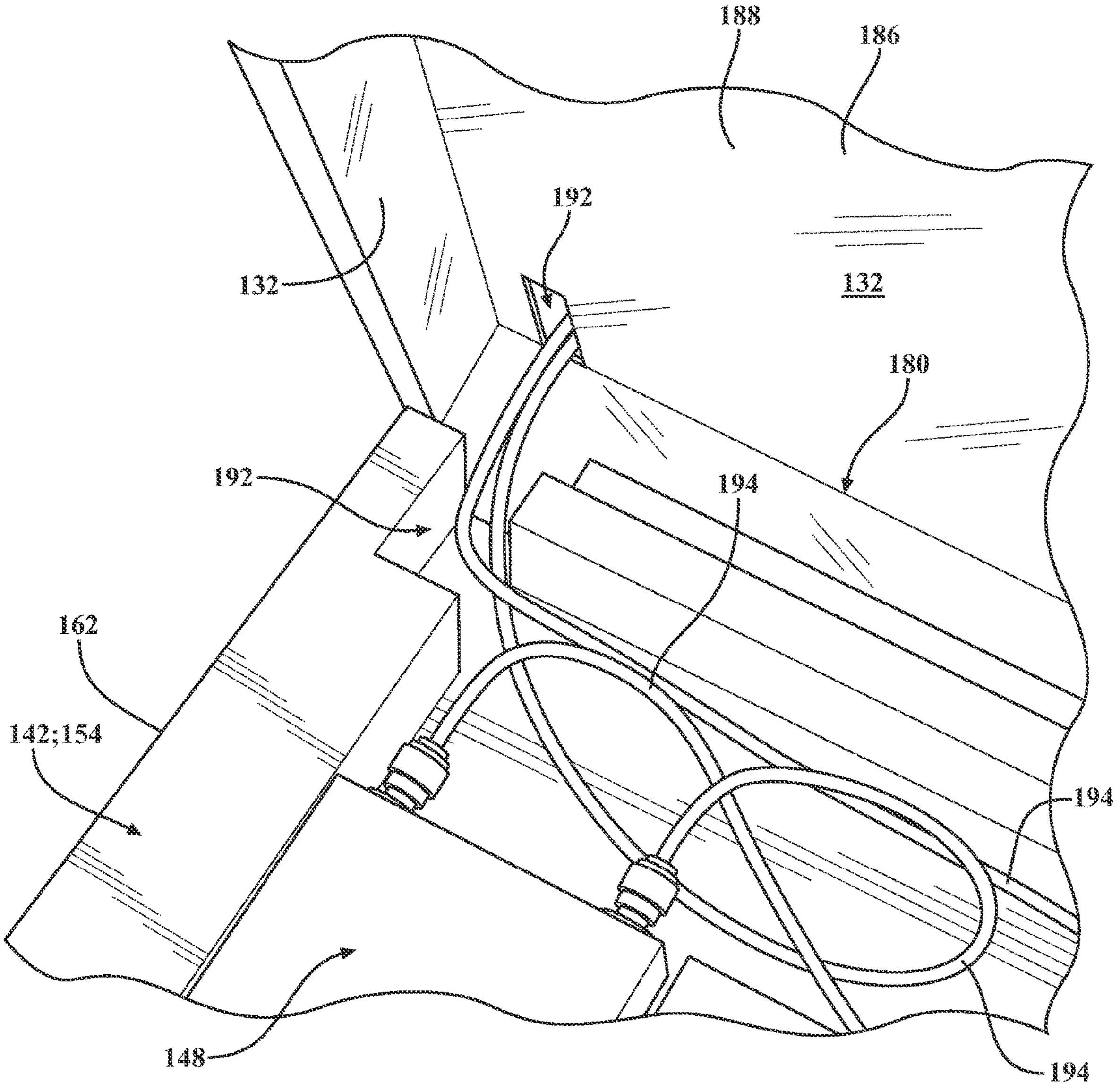
FIG. 14 is a partial perspective view of the tracking assembly of FIGS. 12 and 13, with the tower defining a channel to facilitate routing of wires to the antenna.
Figure 15:
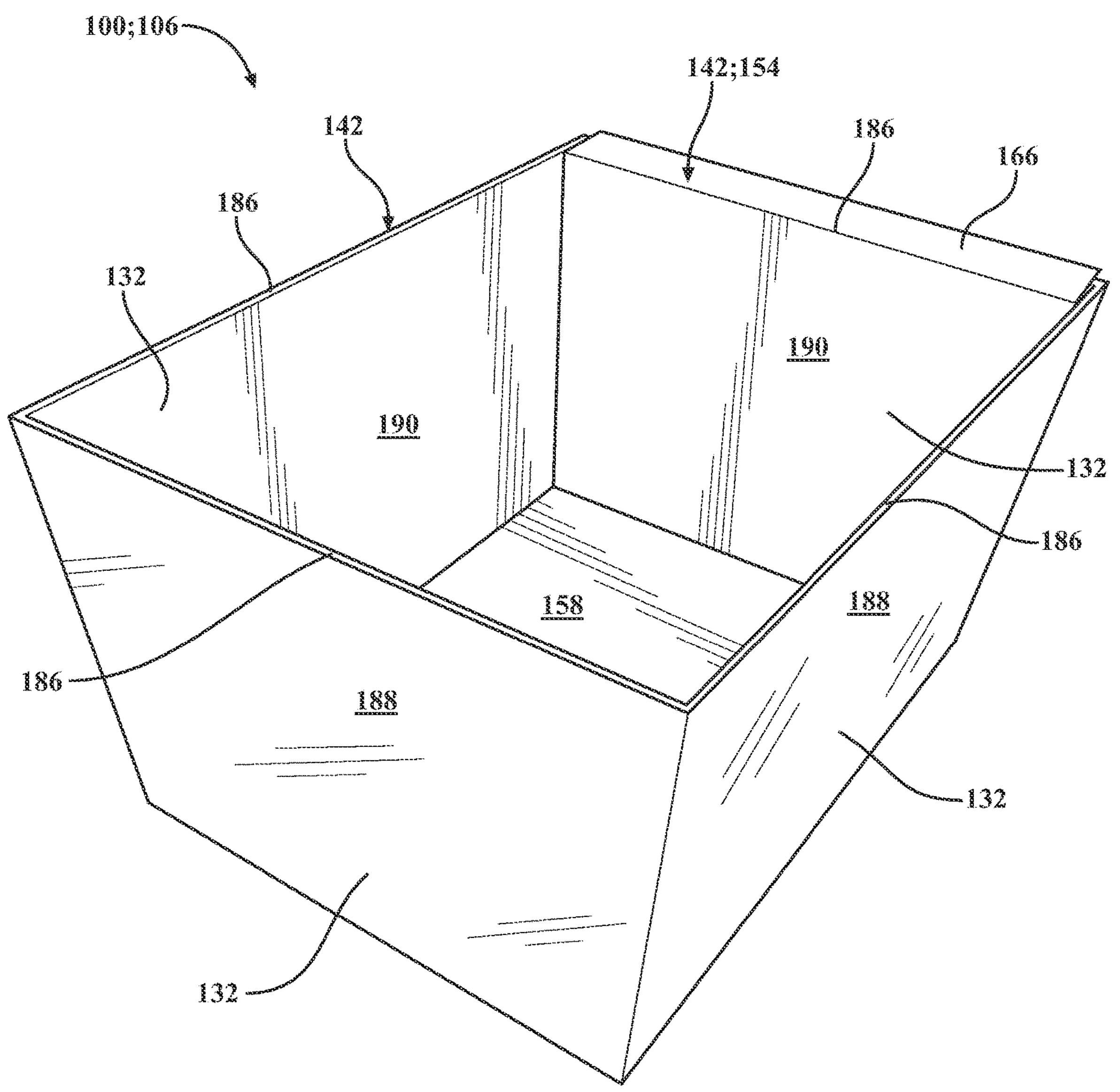
FIG. 15 is a perspective view of the tracking assembly of FIGS. 12-14, with the shield including the interior shield walls, and with the tower disposed exterior to the interior shield walls.

As shown in FIG. 9, the tower frame 162 is provided with a tower window 168 adjacent to the communication interface 146 to facilitate communication across the network 108. Here too, the tower window 168 is arranged so as to be disposed adjacent to and in alignment with the liner window 140 and the shield window 136. As will be appreciated from the subsequent description below, this arrangement allows wireless signals to be exchanged across the network 108 via the communication interface 146 from within the transport container 104 while, at the same time, inhibiting transmission of the wave WV outside of the interior 120 of the transport container 104. The alignment and arrangement of the tower window 168, the liner window 140, the shield window 136, and the communication interface 146 configured laterally and vertically offset relative to one of the interior side walls 130 of the transport container 104. This configuration helps prevent signals from inadvertently being exchanged between two adjacently positioned transport containers 104 during use.

As noted above, the antenna 144 may be realized by two antenna modules 160. The two antenna modules 160 may be supported by the housing 142 adjacent to the lower interior surface 126. Moreover, the system 100, particularly the tracking assembly 106, may further include a foam insert 196 adjacent to the base 152 of the housing 142, and the foam insert 196 may define a recess 198 shaped to receive the antenna 144, particularly the two antenna modules 160. The antenna modules 160 have generally flat, rectangular profiles, and are configured as circular polarized flat panel UHF RFID antenna modules 160. In some versions, the antenna modules 160 may be realized as Times-7 Part Number A6034 antennas. However, other configurations are contemplated, and it will be appreciated that the antenna 144 could instead employ a single antenna module 160, or more than two antenna modules 160, in some versions. By way of non-limiting example, in the representative version depicted in FIG. 5B, two antennas 144 are depicted, each shown generating a respective wave WV. In some versions, each antenna 144 could be configured to generate a respective wave WV according to different parameters (e.g., different scan rates). Other configurations are contemplated. By way of further non-limiting example, in the representative version depicted in FIG. 5C, a single antenna 144 is depicted shown generating the wave WV. Thus, in some versions, the wave WV and/or the functions facilitated by the wave WV could be generated or otherwise defined by a single antenna 144 or by multiple antennas 144. Other configurations are contemplated.

The communication interface 146 is configured to facilitate wireless communication across the network 108. It will be appreciated that the communication interface 146 could communicate according to a number of different protocols, such as 3G, 4G, and/or 5G cellular protocols. However, additional protocols such as WiFi, Bluetooth, Zigbee, and the like are contemplated. Further, the communication interface 146 may also be configured for satellite navigation, such as according to the Global Navigation Satellite System GNSS.

While the communication interface 146 is schematically depicted as a separate component from the controller 148 in the Figures, it will be appreciated that one or more components, systems, and/or devices of the tracking assembly 106 could be integrated together in a common housing and/or on a common circuit, and the like. Furthermore, the communication interface 146 itself may include or otherwise comprise a controller, which could be separate from and connected to the controller 148 coupled to the antenna 144. In some versions, signals received by the communication interface 146 across the network 108 may be utilized to selectively generate the wave WV with the controller 148 (e.g., the communication interface 146 may prompt the controller 148 to generate the wave WV). In some versions, the communication interface 146 may be configured to prompt the controller 148 to generate the wave WV in other ways, such as at predetermined intervals or based on data from one or more types of sensors 170 as described in greater detail below. Here too, it will be appreciated that the controller 148 may be programmed or otherwise configured to generate the wave WV and/or perform other actions without necessarily requiring prompts from the communication interface 146. Other configurations are contemplated.

In some versions, the controller 148 may employ one or more microprocessors for processing instructions or an algorithm stored in memory to control operation of one or more components of the system 100. Additionally or alternatively, the controller 148 may comprise one or more microcontrollers, field programmable gate arrays, systems on a chip, discrete circuitry, and/or other suitable hardware, software, and/or firmware that is capable of carrying out the functions described herein. The controller 148 may comprise one or more subcontrollers configured to control one or more components of the system 100. Other configurations are contemplated.

In some versions, the system further comprises one or more sensors 170 configured to generate data. The sensor 170 is in communication with the controller 148, and the controller 148 is configured to generate the wave WV with the antenna 144 dependent upon the data received from the sensor 170. More specifically, the controller 148 includes or otherwise cooperates with one or more types of sensors 170, such as for example altimeters, accelerometers, gyroscopes, temperature and/or humidity sensors, pressure sensors, and the like. Here, data from one or more sensors 170 may be used to determine when the controller 148 should selectively generate the wave WV. The controller 148 may include an RFID interface 172 configured to selectively sgenerate the wave WV by generating a wave signal WS that is transmitted to the antenna 144. Here, the RFID interface 172 may operate according to RFID Protocol Support EPC global Gen 2V2 (ISO 18000-63). However, other protocols are contemplated.

The battery module 150 powers the controller 148 (and, thus, the communication interface 146), and may configured for replacement or exchange from the tower 154, such as by one or more power connectors 174 coupled to the controller 148 and/or to the communication interface 146. In some versions, the communication interface 146 could be powered via connection with the controller 148. It will be appreciated that power connectors 174 could be of various configurations, types, and/or arrangements. In some versions, the power connectors 174 may be realized as USB cables and the battery module 150 may be provided with USB ports. Other configurations are contemplated. In some versions, the battery module 150 may be configured for connection to a charging station 176 via prongs 178 arranged to facilitate "stackable" charging of multiple battery modules 150 (see FIG. 11; depicted schematically). However, other configurations are contemplated.

In some versions, the controller 148 may be configured to compare one or more operating parameters OP of the battery module 150 (e.g., charging state, voltage, temperature, and the like) relative to one or more predetermined operating parameter thresholds PT to, among other things, determine when the battery module 150 should be charged or otherwise exchanged. To this end, the controller 148 may be configured to generate battery schedule data SD based on comparisons between the operating parameter OP and the predetermined operating parameter threshold PT, and to send the battery schedule data SD across the network 108 to the server 110 or some other remote electronic device 112. Other configurations are contemplated.

It will be appreciated that the network 108, the server 110, and/or the remote electronic devices 112 may be configured or otherwise realized in a number of different ways. By way of non-limiting example, the network 108 could be configured as a 5G cellular network and the server 110 could be realized by one or more types of cloud computing systems, edge computing systems, and/or combinations thereof. The server 110 may employ, include, or otherwise communicate with various interfaces, databases, and the like in order to facilitate collecting, presenting, organizing, and/or evaluating various forms of data. For example, the server 110 may include an interface that is accessible via various types of remote electronic devices 112 (e.g., portable electronic devices such as cell phones, notebook computers, and the like). Other configurations are contemplated.

Referring again, generally, to FIGS. 1-16, as noted above, the system 100 is configured to facilitate remotely tracking various surgical articles 102 stored within transport containers 104 via tracking assemblies 106 in communication with the server 110 across the network 108. It will be appreciated that, depending on the size and quantity of the surgical articles 102 to be supported within the interior 120 of the transport container 104, as well as the physical dimensions of the transport container 104 itself, a number of possible arrangements of different surgical articles 102 may be utilized. Moreover, as surgical articles 102 are removed from (and/or placed into) the interior 120, or otherwise shift in response to movement of the transport container 104, the arrangement may change. Accordingly, the tracking assembly 106 and transport container 104 described and illustrated herein are configured to facilitate reliable, highly-accurate identification of the surgical articles 102 disposed in the interior 120.

The surgical articles 102 may be arranged within the interior 120 with their labels 116 facing upwardly to, among other things, allow logistics representatives or other users of the system 100 to visually identify and distinguish between different surgical articles 102. Here too with this arrangement, the tag 118 is arranged on one of the lateral sides of the box 114. In this way, even when multiple surgical articles 102 are stacked on top of each other within the interior 120, the helically-extending wave WV generated via the antenna 144 can reliably detect all of the tags 118 in order to communicate the identity data ID of each surgical article 102 within the interior 120 to the server 110 across the network 108. In some versions, over one hundred different surgical articles 102 positioned within the interior 120 can be identified accurately in under five seconds. Furthermore, the system 100 is configured such that the battery module 150 can be used to perform periodic scans of the transport container 104 for multiple weeks before requiring a recharge or replacement.

To this end, in some versions, the controller 148 is configured to perform a scan at predetermined intervals of time (e.g., every three hours). The controller 148 may be further configured to selectively generate the wave WV by generating a wave signal WS that is transmitted to the antenna 144, and the controller 148 may be further configured to send the wave signal WS to the antenna 144 at predetermined intervals of time. Once the identity data ID have been transmitted to the server 110 across the network, the tracking assembly 106 may enter a "sleep mode" to conserve power before awaking at the next interval of time and/or until prompted via signals received across the network 108. For example, a user may utilize a remote electronic device 112 to request an accounting of the inventory of a particular transport container 104, whereby a signal transmitted to the communication interface 146 may cause the controller 148 to "wake" and perform a scan between the intervals of time. Here, it will be appreciated that the connectivity to the network 108 via the communication interface 146 (e.g., via a 5G cellular connection) allows the system 100 to routinely and/or selectively (e.g., when prompted) inventory the surgical articles 102 and transmit identity data ID to the server 110 from any location where there is connectivity to the network 108 (e.g., from inside buildings, during transit between locations, and the like).

It will be appreciated that the configurations described above afford significant advantages in connection with inventory management, asset distribution optimization, and interrelated logistics, in that identity data ID and other data stored in or otherwise accessible via the server 110 can be accessed and utilized by multiple users, and in various ways. For example, a logistics representative can remotely check the inventory of one or more transport containers 104 without having to physically access and inspect each surgical article 102 disposed therein. Similarly, logistics representatives could conceivably set various thresholds for particular surgical articles 102, whereby predetermined changes in quantity for a given transport container 104 could be utilized to generate alerts, prompts, and the like (e.g., sent to the remote electronic device 112 assigned to the logistics representative). Similarly, replenished transport containers 104, or additional quantities of certain surgical articles 102, could be automatically shipped to logistics representatives when their inventory falls below a certain threshold.

Moreover, opportunities for decentralized asset distribution are also contemplated, such as where one logistics representative within a particular area or region has an urgent need for a specific surgical article 102 and another logistics representative has an available quantity of that surgical article 102 which are not currently allocated for use (or, potentially, not frequently utilized by that logistics representative). In such circumstances, the system 100 could help facilitate coordination between multiple logistics representatives, with or without intermediary parties (e.g., couriers) to optimize distribution of surgical articles 102. Here too, location data associated with the surgical articles 102 could be utilized (e.g., GNSS location data) to facilitate or otherwise influence coordination of this type. By way of non-limiting example, geofencing could be employed to determine whether or not surgical articles in particular transport containers 104 should be redistributed. Other configurations are contemplated.

Figure 16:
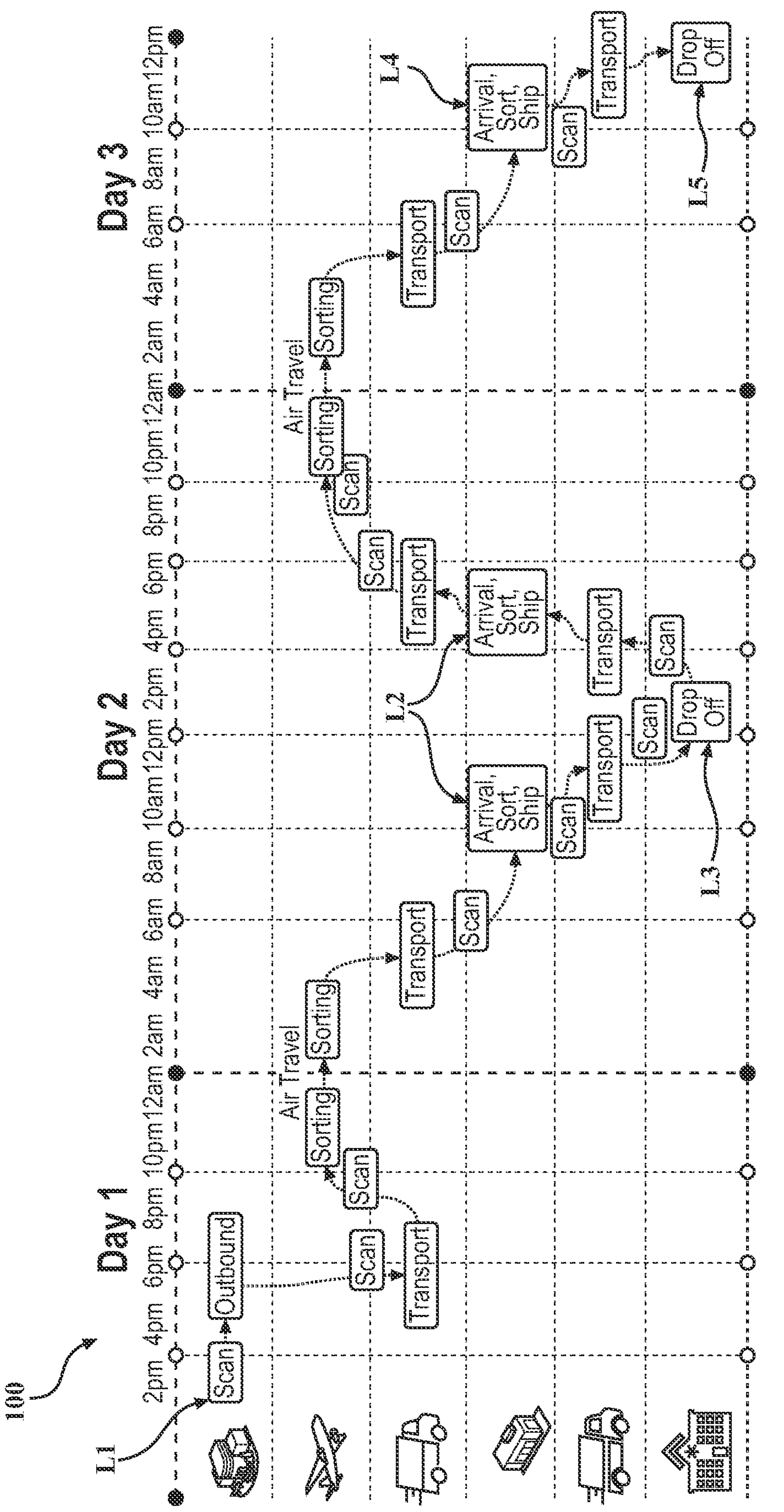
FIG. 16 is a graphical representation of an exemplary journey of a transport container of the system of FIGS. 1-15.

In some versions, data from one or more sensors 170 could be utilized to further optimize power consumption and/or optimization of asset distribution. For example, FIG. 16 depicts an exemplary of a transport container 104 of the system 100. Beginning at an initial location L1 such as a warehouse, the transport container 104 outfitted with the tracking assembly 106 and stocked with an assortment of surgical articles 102 may perform an initial scan to transmit identity data ID to the server 110 at 3:00 PM on Day 1 in this illustrative example. The transport container 104 is loaded onto a courier vehicle headed for an airport. The system 100 is configured to perform scans every three hours unless certain conditions are met as described in greater detail below. During transport in the courier vehicle, another scan is performed at 6:00 PM on Day 1, and identity data ID transmitted to the server 110 while the transport container 104 is in the courier vehicle confirms that no surgical articles 102 have been added or removed from the transport container 104. At 9:00 PM on Day 1, another scan is performed as the transport container 104 is sorted along with other items for transport on an airplane. During air travel, no scans are performed. Here, the system 100 may determine that the transport container 104 is in an airplane via location data (e.g., GNSS location data), and/or based on certain types of sensor data, such as where the sensor 170 is realized as an altimeter. Thus, no scans are performed during air transport.

At 6:00 AM on Day 2, a scan is performed after the transport container 104 has been unloaded from the airplane and is subsequently loaded into a different courier vehicle, which delivers the transport container 104 to a second location L2 such as a regional distribution center. Another scan is performed at 9:00 AM on Day 2, after which a logistics representative loads the transport container 104 into their local vehicle and transports it to a third location L3 such as a city hospital. At 12:00 PM on Day 2, a scan is performed before the local vehicle arrives at the city hospital. The logistics representative removes certain surgical articles 102 from the transport container 104 and delivers them to the city hospital. At 3:00 PM on Day 2, a scan confirms that certain surgical articles 102 have been removed from the transport container 104. At this point, a determination is made that the remaining surgical articles 102 in the transport container 104 should be shipped elsewhere, so the logistics representative travels back to the second location L2 and the transport container 104 is again transported to an airport via a courier vehicle. Scans at 6:00 PM and 9:00 PM confirm that the inventory of the transport container 104 remains unchanged, but once again no scans are performed during air travel.

At 6:00 AM on Day 3, once the transport container 104 has arrived at a different airport and during transit on another courier vehicle to a fourth location L4, such as a different regional distribution center, yet another scan is performed. At 9:00 AM on Day 3, another scan is performed at the fourth location L4, and a different logistics representative takes the transport container to a fifth location L5, such as a rural hospital, to deliver the surgical articles 102. It will be appreciated that the forgoing is an illustrative, non-limiting example of the types of optimization afforded by the system 100 of the present disclosure.

A method for tracking tagged surgical articles 102 across a network 108 is also provided. In one aspect, the method includes the step of providing a transport container 104 defining an interior 120 having a lower interior surface 126, an upper interior surface 128, and a plurality of interior side walls 130 extending between the lower interior surface 126 and the upper interior surface 128. The method also includes the steps of applying a shield 132 to the interior 120 of the transport container 104, inserting a tracking assembly 106 into the interior 120 of the transport container 104, the tracking assembly 106 including an antenna 144, a communication interface 146, and a controller 148, and placing a plurality of tagged surgical articles 102 within the interior 120 of the transport container 104. The method further includes the step of sending, with the controller 148, a wave signal WS to the antenna 144. The method further includes the step of, generating, with the antenna 144 and in response to receiving the wave signal WS, a wave WV extending helically away from the lower interior surface 126 and towards the upper interior surface 128 within the interior 120 of the transport container 104, the wave WV passing through the tagged surgical articles 102 placed within the interior 120 of the transport container 104. The method further includes the step of receiving, with the controller 148 via the antenna 144, identity data ID from each of the plurality of tagged surgical articles 102 placed within the interior 120 of the transport container 104. The method further includes the step of transmitting, with the controller 148 via the communication interface 146, the identity data ID across the network 108.

In another aspect, the method includes providing a transport container 104 defining an interior 120 having a lower interior surface 126, an upper interior surface 128, and plurality of interior side walls 130 extending between the lower interior surface 126 and the upper interior surface 128. The method also includes the steps of applying a shield 132 to the interior 120 of the transport container 104, inserting a tracking assembly 106 into the interior 120 of the transport container 104, the tracking assembly 106 including an antenna 144, a power connector 174, a communication interface 146, and a controller 148, connecting a battery module 150 to the power connector 174 of the tracking assembly 106, and placing a plurality of tagged surgical articles 102 within the interior 120 of the transport container 104. The method further includes the step of sending, with the controller 148, a wave signal WS to the antenna 144. The method further includes the step of generating, with the antenna 144 and in response to receiving the wave signal WS, a wave WV extending helically away from the lower interior surface 126 and towards the upper interior surface 128 within the interior 120 of the transport container 104, the wave WV passing through the tagged surgical articles 102 placed within the interior 120 of the transport container 104. The method further includes the step of receiving, with the controller 148 via the antenna 144, identity data ID from each of the plurality of tagged surgical articles 102 placed within the interior 120 of the transport container 104. The method further includes the step of transmitting, with the controller 148 via the communication interface 146, the identity data ID across the network 108.

The method further includes the step of comparing, with the controller 148, an operating parameter of the battery module 150 relative to a predetermined operating parameter threshold. The method further includes the step of generating, with the controller 148, battery schedule data based on a comparison between the operating parameter and the predetermined operating parameter threshold. The method further includes the step of sending, with the controller 148 via the communication interface 146, the battery schedule data across the network 108.

Either aspect of the method may further require the step of sending, with the controller 148, a wave signal WS to the antenna 144 to be completed at predetermined intervals of time. Moreover, either aspect of the method may further include the step of transmitting a signal to the communication interface 146 to cause the controller 148 to send the wave signal WS to the antenna 144. Further, in either aspect of the method, the tracking assembly 106 may further include a sensor 170 in communication with the controller 148, and may further include the step(s) of generating data with the sensor 170 and sending the data to the controller 148. Further still, in either aspect of the method, the step of sending, with the controller 148, a wave signal WS to the antenna 144 may be dependent upon the data received from the sensor 170. Even further still, either aspect of the method may further include the step of transmitting, with the controller 148 via the communication interface 146, alerts in response to predetermined changes in identity data ID received with the controller 148 via the antenna 144.

It will be further appreciated that the terms “include,” “includes,” and “including” have the same meaning as the terms “comprise,” “comprises,” and “comprising.”

Several versions have been discussed in the foregoing description. However, the versions discussed herein are not intended to be exhaustive or limit the invention to any particular form. The terminology which has been used is intended to be in the nature of words of description rather than of limitation. Many modifications and variations are possible in light of the above teachings and the embodiments may be practiced otherwise than as specifically described. Moreover, two or more of the versions disclosed herein may be combined with or without modification.

The present disclosure also comprises the following clauses, with specific features laid out in dependent clauses, that may specifically be implemented as described in greater detail with reference to the configurations and drawings above.

CLAUSES

I. A system for tracking tagged surgical articles across a network, the system comprising:
- a transport container defining an interior having a lower interior surface, an upper interior surface, and a plurality of interior side walls extending between the lower interior surface and the upper interior surface; and
- a tracking assembly including a housing shaped to be received within the interior of the transport container, an antenna supported by the housing adjacent to the lower interior surface and being arranged to selectively generate a wave extending helically away from the lower interior surface and towards the upper interior surface within the interior of the transport container, a communication interface for wirelessly communicating with the network, and a controller coupled to the housing and disposed in electrical communication with the antenna and the communication interface, the controller being configured to:
- generate the wave with the antenna to scan the interior of the transport container for tagged surgical articles,
- receive identity data from each of the tagged surgical articles with the antenna in response to generating the wave, and transmit the identity data across the network via the communication interface.

II. The system as set forth in clause I, wherein the tracking assembly further includes a shield arranged to block waves generated by the antenna from exiting the transport container.

III. The system as set forth in any one of clauses I-II, wherein the housing includes a base adjacent to the lower interior surface of the transport container, and wherein the housing includes a tower coupled to the base and extending away from the lower interior surface of the transport container.

IV. The system as set forth in any one of clauses I-III, wherein the tower defines a tower interior, and wherein the communication interface and the controller are operatively attached to the tower and supported in the tower interior.

V. The system as set forth in any one of clauses I-IV, wherein the base includes a base frame supporting the antenna and a base cover coupled to the base frame and selectively moveable relative to the base frame to permit access to the antenna.

VI. The system as set forth in any one of clauses I-V, wherein the shield is adjacent to the base frame and the tower.

VII. The system as set forth in any one of clauses I-VI, wherein the shield is disposed in spaced relation from the base cover to permit waves generated with the antenna to scan the interior of the transport container for tagged surgical articles.

VIII. The system as set forth in any one of clauses I-VII, wherein the shield includes at least one chosen from a lower shield surface arranged to block waves generated by the antenna from exiting the lower interior surface of the transport container, an upper shield surface arranged to block waves generated by the antenna from exiting the upper interior surface of the transport container, and interior shield walls arranged to block waves generated by the antenna from exiting the interior side walls of the transport container.

IX. The system as set forth in any one of clauses I-VIII, wherein the shield includes the interior shield walls, and wherein the interior shield walls are disposed about the tower.

X. The system as set forth in any one of clauses I-IX, wherein the shield defines a shield window arranged relative to the communication interface to facilitate transmittal of the identity data across the network via the communication interface.

XI. The system as set forth in any one of clauses I-X, wherein the shield includes the interior shield walls, and wherein the tower is disposed exterior to the interior shield walls.

XII. The system as set forth in any one of clauses I-XI, wherein the housing defines a slot sized to permit the base cover to selectively move relative to the base frame to permit access to the antenna.

XIII. The system as set forth in any one of clauses I-XII further comprising at least one battery module configured to power the controller.

XIV. The system as set forth in any one of clauses I-XIII, wherein the housing includes a base adjacent to the lower interior surface of the transport container, and a tower coupled to the base, extending away from the lower interior surface of the transport container, and defining a tower interior, with the at least one battery module operatively attached to the tower and supported in the tower interior.

XV. The system as set forth in any one of clauses I-XIV, wherein the housing includes exterior surfaces facing the transport container, and wherein the shield is disposed on the exterior surfaces of the housing.

XVI. The system as set forth in any one of clauses I-XV, wherein the housing includes interior surfaces defining a housing interior, and wherein the shield is disposed on the interior surfaces of the housing.

XVII. The system as set forth in any one of clauses I-XVI further comprising a sensor configured to generate data, wherein the sensors is in communication with the controller, and wherein the controller is configured to generate the wave with the antenna dependent upon the data received from the sensor.

XVIII. The system as set forth in any one of clauses I-XVII, wherein the controller is further configured to selectively generate the wave by generating a wave signal that is transmitted to the antenna, and wherein the controller is further configured to send the wave signal to the antenna at predetermined intervals of time.

XIX. The system as set forth in any one of clauses I-XVIII, wherein the antenna is configured as a circular polarized flat panel ultra-high frequency (UHF) radio-frequency identification (RFID) antenna module.

XX. The system as set forth in any one of clauses I-XIX, wherein the communication interface is configured to transmit the identity data across the network according to at least one chosen from IIIG, IVG, and/or VG cellular protocols.

XXI. The system as set forth in any one of clauses I-XX, wherein the shield includes a liner.

XXII. The system as set forth in any one of clauses I-XXI, wherein the liner defines a liner window in alignment with the shield window and arranged relative to the communication interface to facilitate transmittal of the identity data across the network via the communication interface.

XXIII. The system as set forth in any one of clauses I-XXII, wherein the tower defines a tower window in alignment with the shield window and arranged relative to the communication interface to facilitate transmittal of the identity data across the network via the communication interface.

XXIV. The system as set forth in any one of clauses I-XXIII, wherein the tower window is in alignment with the liner window.

XXV. The system as set forth in any one of clauses I-XXIV, wherein the tower defines a channel to facilitate routing of wires between at least one chosen from the communication interface, the controller, and the battery module to the antenna.

XXVI. The system as set forth in any one of clauses I-XXV, wherein the antenna includes two antenna modules supported by the housing adjacent to the lower interior surface.

XXVII. The system as set forth in any one of clauses I-XXVI, wherein the upper interior surface of the transport container includes interlocking flaps pivotably coupled to the plurality of interior side walls.

XXVIII. The system as set forth in any one of clauses I-XXVII, wherein the tower is pivotably coupled to the base of the housing.

XXIX. The system as set forth in any one of clauses I-XXVIII further comprising a foam insert adjacent to the base of the housing.

XXX. The system as set forth in any one of clauses I-XXIX, wherein the foam insert defines a recess shaped to receive the antenna.

XXXI. The system as set forth in any one of clauses I-XXX, wherein the antenna is configured to generate the wave in a helical configuration.

XXXII. A method for tracking tagged surgical articles across a network, the method comprising:

providing a transport container defining an interior having a lower interior surface, an upper interior surface, and a plurality of interior side walls extending between the lower interior surface and the upper interior surface;

applying a shield to the interior of the transport container;

inserting a tracking assembly into the interior of the transport container, the tracking assembly including an antenna, a communication interface, and a controller;

placing a plurality of tagged surgical articles within the interior of the transport container;

sending, with the controller, a wave signal to the antenna;

generating, with the antenna and in response to receiving the wave signal, a wave extending helically away from the lower interior surface and towards the upper interior surface within the interior of the transport container, the wave passing through the tagged surgical articles placed within the interior of the transport container;

receiving, with the controller via the antenna, identity data from each of the plurality of tagged surgical articles placed within the interior of the transport container; and transmitting, with the controller via the communication interface, the identity data across the network.

XXXIII. A method for tracking tagged surgical articles across a network, the method comprising:

providing a transport container defining an interior having a lower interior surface, an upper interior surface, and a plurality of interior side walls extending between the lower interior surface and the upper interior surface;

applying a shield to the interior of the transport container;

inserting a tracking assembly into the interior of the transport container, the tracking assembly including an antenna, a power connector, a communication interface, and a controller;

connecting a battery module to the power connector of the tracking assembly;

placing a plurality of tagged surgical articles within the interior of the transport container;

sending, with the controller, a wave signal to the antenna;

generating, with the antenna and in response to receiving the wave signal, a wave extending helically away from the lower interior surface and towards the upper interior surface within the interior of the transport container, the wave passing through the tagged surgical articles placed within the interior of the transport container;

receiving, with the controller via the antenna, identity data from each of the plurality of tagged surgical articles placed within the interior of the transport container;

transmitting, with the controller via the communication interface, the identity data across the network;

comparing, with the controller, an operating parameter of the battery module relative to a predetermined operating parameter threshold;

generating, with the controller, battery schedule data based on a comparison between the operating parameter and the predetermined operating parameter threshold; and sending, with the controller via the communication interface, the battery schedule data across the network.

XXXIV. The method as set forth in any one of clauses XXXII-XXXIII, wherein the step of sending, with the controller, a wave signal to the antenna is completed at predetermined intervals of time.

XXXV. The method as set forth in any one of clauses XXXII-XXXIV further comprising transmitting a signal to the communication interface to cause the controller to send the wave signal to the antenna.

XXXVI. The method as set forth in any one of clauses XXXII-XXXV, wherein the tracking assembly further includes a sensor in communication with the controller, and further comprising generating data with the sensor and sending the data to the controller.

XXXVII. The method as set forth in any one of clauses XXXII-XXXVI wherein the step of sending, with the controller, a wave signal to the antenna is dependent upon the data received from the sensor.

XXXVIII. The method as set forth in any one of clauses XXXII-XXXVII further comprising transmitting, with the controller via the communication interface, alerts in response to predetermined changes in identity data received with the controller via the antenna.

What is claimed is:

1. A system for tracking tagged surgical articles across a network, the system comprising:

a transport container defining an interior having a lower interior surface, an upper interior surface, and a plurality of interior side walls extending between the lower interior surface and the upper interior surface; and a tracking assembly including:

a housing shaped to be received within the interior of the transport container and including a base adjacent to the lower interior surface of the transport container and a tower coupled to the base and extending away from the lower interior surface of the transport container, an antenna supported by the housing adjacent to the lower interior surface and being arranged to selectively generate a wave extending helically away from the lower interior surface and towards the upper interior surface within the interior of the transport container, a shield arranged to block waves generated by the antenna from exiting the transport container, a communication interface for wirelessly communicating with the network, and a controller coupled to the housing and disposed in electrical communication with the antenna and the communication interface, the controller being configured to:

generate the wave with the antenna to scan the interior of the transport container for tagged surgical articles, receive identity data from each of the tagged surgical articles with the antenna in response to generating the wave, and transmit the identity data across the network via the communication interface; and wherein the base includes a base frame supporting the antenna and a base cover coupled to the base frame and selectively moveable relative to the base frame to permit access to the antenna.

2. The system as set forth in claim 1, wherein the tower defines a tower interior, and wherein the communication interface and the controller are operatively attached to the tower and supported in the tower interior.

3. The system as set forth in claim 1, wherein the shield is adjacent to the base frame and the tower.

4. The system as set forth in claim 1, wherein the shield is disposed in spaced relation from the base cover to permit waves generated with the antenna to scan the interior of the transport container for tagged surgical articles.

5. The system as set forth in claim 1, wherein the shield includes at least one chosen from a lower shield surface arranged to block waves generated by the antenna from exiting the lower interior surface of the transport container, an upper shield surface arranged to block waves generated by the antenna from exiting the upper interior surface of the transport container, and interior shield walls arranged to block waves generated by the antenna from exiting the interior side walls of the transport container.

6. The system as set forth in claim 5, wherein the shield includes the interior shield walls, and wherein the interior shield walls are disposed about the tower.

7. The system as set forth in claim 6, wherein the shield defines a shield window arranged relative to the communication interface to facilitate transmittal of the identity data across the network via the communication interface.

8. The system as set forth in claim 5, wherein the shield includes the interior shield walls, and wherein the tower is disposed exterior to the interior shield walls.

9. The system as set forth in claim 8, wherein the housing defines a slot sized to permit the base cover to selectively move relative to the base frame to permit access to the antenna.

10. The system as set forth in claim 1, further comprising at least one battery module configured to power the controller.

11. The system as set forth in claim 10, wherein the housing includes a base adjacent to the lower interior surface of the transport container, and a tower coupled to the base, extending away from the lower interior surface of the transport container, and defining a tower interior, with the at least one battery module operatively attached to the tower and supported in the tower interior.

12. The system as set forth in claim 1, wherein the housing includes exterior surfaces facing the transport container, and wherein the shield is disposed on the exterior surfaces of the housing.

13. The system as set forth in claim 1, wherein the housing includes interior surfaces defining a housing interior, and wherein the shield is disposed on the interior surfaces of the housing.

14. The system as set forth in claim 1, further comprising a sensor configured to generate data, wherein the sensor is in communication with the controller, and wherein the controller is configured to generate the wave with the antenna dependent upon the data received from the sensor.

15. The system as set forth in claim 1, wherein the controller is further configured to selectively generate the wave by generating a wave signal that is transmitted to the antenna, and wherein the controller is further configured to send the wave signal to the antenna at predetermined intervals of time.

16. The system as set forth in claim 1, wherein the antenna is configured as a circular polarized flat panel ultra-high frequency (UHF) radio-frequency identification (RFID) antenna module.

17. The system as set forth in claim 1, wherein the communication interface is configured to transmit the identity data across the network according to a cellular protocol.

* * * * *